United States Patent
Francis et al.

[11] Patent Number: 5,824,661
[45] Date of Patent: Oct. 20, 1998

[54] SULFUR-CONTAINING PHOSPHONATE COMPOUNDS, PHARMACEUTICAL COMPOSITIONS, AND METHODS OF TREATING ABNORMAL CALCIUM AND PHOSPHATE METABOLISM

[75] Inventors: Marion David Francis, Cincinnati, Ohio; Susan Mary Kaas, Norwich, N.Y.; Frank Hallock Ebetino, Cincinnati, Ohio

[73] Assignee: The Procter & Gamble Company, Cincinnati, Ohio

[21] Appl. No.: 301,514

[22] Filed: Sep. 7, 1994

Related U.S. Application Data

[63] Continuation of Ser. No. 891,309, May 29, 1992, abandoned.

[51] Int. Cl.$^6$ .......... A61K 31/66; A61K 31/665; A61K 31/675; C07F 9/65
[52] U.S. Cl. .......... 514/75; 514/102; 514/107; 514/108; 514/120; 514/121; 514/155; 548/187; 548/189; 549/29; 549/77; 549/80; 549/218; 558/173; 558/179; 558/180; 558/231; 558/232; 562/8; 562/11; 562/15; 562/21
[58] Field of Search .......... 514/75, 102, 107, 514/108, 120, 121, 155; 558/173, 179, 180, 231, 232; 562/8, 11, 15, 12, 13, 14, 21; 548/187, 189; 549/29, 77, 80, 218

[56] References Cited

U.S. PATENT DOCUMENTS

| | | | |
|---|---|---|---|
| 4,208,401 | 6/1980 | Bauman | 424/54 |
| 4,267,108 | 5/1981 | Blum et al. | 260/326.61 |
| 4,407,761 | 10/1983 | Blum et al. | 260/502.5 C |
| 4,687,768 | 8/1987 | Benedict et al. | 514/102 |
| 4,746,654 | 5/1988 | Breliere et al. | 514/108 |
| 4,784,993 | 11/1988 | Bosies et al. | 514/93 |
| 4,868,164 | 9/1989 | Ebetino et al. | 514/80 |
| 4,876,247 | 10/1989 | Barbier et al. | 514/89 |
| 4,876,248 | 10/1989 | Breliere et al. | 514/108 |
| 4,922,007 | 5/1990 | Kieczykowksi et al. | 562/13 |
| 4,933,472 | 6/1990 | Isomura et al. | 549/218 |
| 4,939,130 | 7/1990 | Jaeggi et al. | 514/94 |
| 4,939,131 | 7/1990 | Benedict et al. | 514/102 |
| 4,971,958 | 11/1990 | Bosies et al. | 514/89 |
| 5,071,840 | 12/1991 | Ebetino et al. | 514/89 |
| 5,104,863 | 4/1992 | Benedict et al. | 514/80 |
| 5,137,880 | 8/1992 | Ebetino et al. | 514/80 |

FOREIGN PATENT DOCUMENTS

| | | | |
|---|---|---|---|
| A-26738/88 | 6/1989 | Australia | C07F 9/38 |
| A-45467/89 | 5/1990 | Australia | C07F 9/38 |
| 0100718 | 2/1984 | European Pat. Off. | |
| 0170228 | 2/1986 | European Pat. Off. | C07F 9/38 |
| 0186405 | 7/1986 | European Pat. Off. | C07F 9/547 |
| 0298553 | 1/1989 | European Pat. Off. | C07F 9/38 |
| 0 594 857 A1 | 5/1994 | European Pat. Off. | C07F 9/38 |
| 4011777 | 10/1990 | Germany . | |
| WO 90/12017 | 10/1990 | WIPO | C07F 9/653 |
| WO 91/10646 | 7/1991 | WIPO | C07D 205/04 |

Primary Examiner—Yogendra N. Gupta
Attorney, Agent, or Firm—Richard A. Hake; Karen F. Clark; Carl J. Roof

[57] ABSTRACT

Compounds of the formula

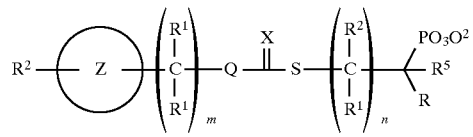

where m and n are integers 0 to 10 and m+n equals 0 to 10,
(a) X is O or S
(b) Z is a covalent bond; a monocyclic or polycyclic carbocycle ring moiety; or a monocyclic or polycyclic heterocyclic ring moiety containing one or more heteroatoms selected from O, S, or N;
(c) Q is covalent bond; O; or S;
(d) R is COOH, $SO_3H$, $PO_3H_2$, or $P(O)(OH)R^4$, wherein $R^4$ is $C_1$–$C_8$ alkyl;
(e) $R^1$, $R^2$ and $R^5$ are as defined in the claims.

are useful in the treatment of calcium and phosphate elated disorders, such as arthritis and the like.

14 Claims, No Drawings

SULFUR-CONTAINING PHOSPHONATE COMPOUNDS, PHARMACEUTICAL COMPOSITIONS, AND METHODS OF TREATING ABNORMAL CALCIUM AND PHOSPHATE METABOLISM

This is a continuation of application Ser. No. 07/891,309, filed on May 29, 1992, now abandoned.

BACKGROUND OF INVENTION

This invention relates to novel sulfur-containing, phosphonate compounds, including bisphosphonates, phosphonoalkylphosphinates, phosphonocarboxylates, and phosphonosulfonates. This invention further relates to pharmaceutical compositions containing these novel compounds, as well as to a method of treating or preventing certain metabolic bone disorders characterized by abnormal calcium and phosphate metabolism, utilizing a compound or pharmaceutical composition of the present invention. In addition, this invention relates to a method of osteoprotective treatment or prevention of arthritis, especially rheumatoid arthritis and osteoarthritis, utilizing various compounds disclosed herein. Specifically, this invention relates to a method of treating or preventing osteoporosis and arthritis, especially rheumatoid arthritis and osteoarthritis, by utilizing a compound or pharmaceutical composition of the present invention.

A number of pathological conditions which can afflict warm-blooded animals involves abnormal calcium and phosphate metabolism. Such conditions may be divided into two broad categories.

1. Conditions which are characterized by anomalous mobilization of calcium and phosphate leading to general or specific bone loss, such as osteoporosis and Paget's disease; or excessively high calcium and phosphate levels in the fluids of the body, such as hypercalcemia of malignancy. Such conditions are sometimes referred to herein as pathological hard tissue demineralizations.

2. Conditions which cause or result from deposition of calcium and phosphate anomalously in the body, such as rheumatoid arthritis and osteoarthritis. These conditions are sometimes referred to herein as pathological calcifications.

The first category included the most common metabolic bone disorder, osteoporosis; osteoporosis is a condition in which bone hard tissue is lost disproportionately to the development of new hard tissue. Osteoporosis can be generally defined as the reduction in the quantity of bone, or the atrophy of skeletal tissue. Marrow and bone spaces become larger, fibrous binding decreases, and compact bone becomes fragile. Osteoporosis can be subclassified as menopausal, senile, drug-induced (e.g. adreno-corticoid, as can occur in steroid therapy); disease-induced (arthritic and tumor), etc.; however, the manifestations are essentially the same. In general, there are two types of osteoporosis: primary and secondary. "Secondary osteoporosis" is the result of a separate identifiable disease process or agent. However, approximately 90% of all osteoporosis cases are "primary osteoporosis". Such primary osteoporosis includes postmenopausal osteoporosis, disuse osteoporosis, age-associated osteoporosis (affecting a majority of individuals over the age of 70 to 80), and idiopathic osteoporosis, affecting middle-aged and younger men and women.

For some osteoporotic individuals, the loss of bone tissue is sufficiently great so as to cause mechanical failure of the bone structure. Bone fractures often occur, for example, in the hip and spine of women suffering from postmenopausal osteoporosis. Kyphosis (abnormally increased curvature of the thoracic spine) may also result.

The mechanism of bone loss in osteoporotics is believed to involve an imbalance in the process of "bone remodeling". Bone remodeling occurs throughout life, renewing the skeleton and maintaining the strength of bone. This remodeling involves the erosion and filling of discrete sites on the surface of bones, by an organized group of cells called "basic multicellular units" or "BMUs". BMUs primarily consist of "osteoclasts", "osteoblasts", and their cellular precursors. In the remodeling cycle, bone is resorbed at the site of an "activated" BMU by an osteoclast, forming a resorption cavity. This cavity is then filled with bone by an osteoblast.

Normally, in adults, the remodeling cycle results in a small deficit in bone, due to incomplete filling of the resorption cavity. Thus, even in healthy adults, age-related bone loss occurs. However, in osteoporotics, there may be an increase in the number of BMUs that are activated. This increased activation accelerates bone remodeling, resulting in abnormally high bone loss.

Although its etiology is not fully understood, there are many risk factors thought to be associated with osteoporosis. These include low body weight, low calcium intake, physical inactivity, and estrogen deficiency.

Current osteoporosis treatment largely consists of calcium and estrogen administration.

The second category, involving conditions manifested by anomalous calcium and phosphate deposition, includes myositis ossificans progressive, calcinosis universalis, and such afflictions as arthritis (including, for example, rheumatoid arthritis and osteoarthritis), neuritis, bursitis, tendonitis, and other conditions which predispose involved tissue to deposition of calcium.

In addition to osteoporosis, bone loss can result from rheumatoid arthritis and osteoarthritis. Rheumatoid arthritis is a chronic, systemic and articular inflammatory disorder characterized by weakening of the joint capsules and ligaments, followed by destruction of cartilage, ligaments, tendon and bone, and a decrease in viscosity and other alterations in the synovial fluid. Rheumatoid arthritis symptoms include systemic weakness, fatigue, localized pain, stiffness and weakness and swelling and deformation of the joints of the body. Rheumatoid arthritis is most common in women in the fourth to sixth decade of life.

The pathogenesis of rheumatoid arthritis, leading to the destruction of the joints, is characterized by two phases: 1) an exudative phase involving the microcirculation and the synovial cells that allow an influx of plasma proteins and cellular elements into the joint and 2) a chronic inflammatory phase occurring in the sub-synovium and subchondral bone, characterized by pannus (granulation tissue) formation in the joint space, bone erosion, and cartilage destruction. The pannus may form adhesions and scar tissue which causes the joint deformities characteristic of rheumatoid arthritis.

The etiology of rheumatoid arthritis remains obscure. Infectious agents such as bacteria and viruses have been implicated. A current hypothesis is that the Epstein-Barr (EBV) virus is a causative agent for rheumatoid arthritis.

Current rheumatoid arthritis treatment consists predominantly of symptomatic relief by administration of non-steroidal anti-inflammatory drugs. Non-steroidal anti-inflammatory drug treatment is mainly effective in the early stages of rheumatoid arthritis; it is unlikely it will produce suppression of joint inflammation if the disease is present for more than one year. Gold, methotrexate, immunosuppressants and corticosteroids have been tried with limited success.

On the other hand, osteoarthritis is an inherently non-inflammatory disorder of the movable joints characterized by deterioration and abrasion of articular cartilage, as well as by formation of new bone at the joint surface. As osteoarthritis progresses, the surface of the articular cartilage is disrupted and wear particles gain access to the synovial fluid which in turn stimulates phagocytosis by macrophage cells. Thus, an inflammatory response is eventually induced in osteoarthritis. Common clinical symptoms of osteoarthritis include cartilaginous and bony enlargements of the finger joints and stiffness on awakening, and pain movement.

Common symptomatic treatments for osteoarthritis include analgesics, anti-inflammatories, steroids, and physical therapy.

A variety of phosphonic acid derivatives have been proposed for use in the treatment and prophylaxis of diseases involving abnormal calcium and phosphate metabolism. For example, numerous references, all incorporated by reference herein, disclose compositions containing polyphosphonates, in particular bisphosphonates such as ethane-1-hydroxy-1, 1-diphosphonic acid ("EHDP"), and their use in inhibiting anomalous deposition and mobilization of calcium and phosphate in animal tissue: U.S. Pat. No. 3,683,080, issued Aug. 8, 1972 and U.S. Pat. No. 4,230,700, issued Oct. 28, 1980, both to Francis, and U.S. Pat. No. 4,868,164 to Ebetino, issued Sep. 19, 1989. Numerous other references describe heterocyclic-substituted diphosphonic acids useful for the treatment of osteoporosis and/or arthritis, and are hereby incorporated by reference herein: U.S. Pat. No. 4,868,164, to Ebetino, et al., issued Sep. 19, 1989; U.S. Pat. No. 5,104,863, to Benedict, et al., issued Apr. 14, 1992; U.S. Pat. No. 4,267,108, to Blum et al., issued May 12, 1981; European Patent Application Publication of Boehringer Mannheim GmbH No. 170,228, published Feb. 5, 1986; European Patent Application Publication No. 186,405, of Benedict and Perkins, published Jul. 2, 1986 ; U.S. Pat. No. 4,754,993, Bosies, et al. issued Nov. 15, 1988; U.S. Pat. No. 4,939,130, Jaeggi, et al., issued Jul. 3, 1990; U.S. Pat. No. 4,971,958, Bosies, et al., issued Nov. 20, 1990; DE 40 11 777, Jaeggi, K., published Oct. 18, 1990; WO 90/12017, of Dunn, et al., published Oct. 18, 1990; WO 91/10646, Youssefyeh, R., et al., published Jul. 25, 1991; AU-A-26738/88, Jaeggi, published Jun. 15, 1989, AU-A-45467/89 (assigned to Ciba-Geigy), published May 31, 1990; and U.S. Pat. No. 4,208,401 to Bauman issued Jun. 17, 1980.

Further, European Patent 0,298,553 to Ebetino, published Jan. 11, 1989, describes thiol-substituents amongst a myriad of other substituents, for suitable as substituents on methylene phosphonoalkylphosphinic acids. There is no teaching therein, however, that a thiol substituent increases antiresorptive and antiarthritis activity over the numerous other substituents disclosed.

In addition, several references describe sulfur-containing phosphonic acids which are said to be useful in the treatment of inflammation symptoms, See e.g. U.S. Pat. No. 4,746,654 to Breliere et al. (assigned to Sanofi), issued May 24, 1988; and EPO 100,718 to Breliere et al. (assigned to Sanofi), published Feb. 15, 1984.

Further, U.S. Pat. No. 4,876,247 to Barbier et al. (assigned to Sanofi), issued Oct. 24, 1989 describes sulfur-containing methylenediphosphonic acid derivatives useful in the treatment of complaints due to inflammatory phenomena and especially for the treatment of arthritic conditions. Also, U.S. Pat. No. 5,071,840 to Ebetino et al., issued Dec. 10, 1991, discloses sulfur-containing heterocycle-substituted diphosphonates in which the diphosphonate-substituted carbon moiety is attached to a carbon atom in a nitrogen-containing six-membered ring heterocycle. The compounds described therein are useful in the treatment of conditions involving abnormal calcium and phosphate metabolism, specifically osteoporosis and arthritis.

None of these references disclose the utility of a sulfur-containing bisphosphonate compound wherein the sulfur-containing chain has a carbonyl carbon. Further, none of these references disclose the utility of a thio-substituted, phosphonate compound in preventing and treating osteoporosis and rheumatoid arthritis and osteoarthritis. The thio-substituents defined herein include thiol, alkyl thiols, thioesters, alkyl thioesters, dithioesters and alkyl dithioesters, thiocarbamates, alkyl thiocarbamates, dithiocarbamates, alkyl dithiocarbamates, thiocarbonates, alkyl thiocarbonates, dithiocarbonate, and alkyl dithiocarbonates.

In addition, the compounds disclosed herein have osteoprotective activity at the site of joint destruction in arthritic conditions and have that activity as an additional benefit in the treatment of arthritis over the above merely relieving the symptoms of inflammation. The term "osteoprotective activity" as used herein means disease-modifying activity on bone and surrounding soft tissue at the site of joint destruction.

It has been surprisingly discovered that the compounds of the present invention have more potent bone antiresorptive activity, and also greater therapeutic utility in treating osteoporosis and arthritis, than heterocyclic bisphosphonate compounds not having a thio-substituent.

It is therefore an object of the present invention to provide new, more potent compounds which are potent bone resorption inhibiting agents useful in osteoporosis therapy and anti-arthritic agents useful in the treatment of osteoarthritis and rheumatoid arthritis. It is a further object of the present invention to provide pharmaceutical compositions useful for the treatment and prophylaxis of abnormal calcium and phosphate metabolism and for the treatment and prophylaxis of arthritis, especially rheumatoid arthritis and osteoarthritis. In addition, it is an object of the present invention to provide methods for treating or preventing diseases characterized by abnormal calcium and phosphate metabolism in humans or other mammals, including osteoporosis, and arthritis, especially rheumatoid arthritis and osteoarthritis.

These and other objects of the present invention will become apparent from the detailed disclosure of the present invention provided hereinafter.

SUMMARY OF THE INVENTION

The present invention relates to novel sulfur-containing phosphonate compounds and novel thio-substituted compounds, including bisphosphonates, phosphonoalkylphosphonates, phosphonocarboxylates, and phosphonosulfonates, and the pharmaceutically-acceptable salts and esters thereof. The present invention further relates to pharmaceutical compositions containing a safe and effective amount of a compound of the present invention, and pharmaceutically-acceptable excipients. Finally, the present invention relates to methods for osteoprotective treatment and prevention of pathological conditions characterized by abnormal calcium and phosphate metabolism in humans or other mammals, including treating or preventing osteoporosis and arthritis, especially rheumatoid arthritis and osteoarthritis. This method comprises administering to a human or other mammal in need of such treatment of a safe and effective amount of a compound or composition of the present invention. These compounds have the following general structure:

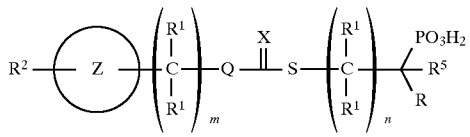

wherein m and n are integers 0 to 10 and m+n equals 0 to 10, and wherein (a) X is O or S;

(b) Z is a covalent bond; a monocyclic or polycyclic carbocyclic ring moiety; or a monocyclic or polycyclic heterocyclic ring moiety containing one or more heteroatoms selected from O, S, or N;

(c) Q is covalent bond; O; or S;

(d) R is $COOH$, $SO_3H$, $PO_3H_2$, or $P(O)(OH)R^4$, wherein $R^4$ is substituted or unsubstituted $C_1$–$C_8$ alkyl;

(e) each $R^1$ is independently selected from —$SR^6$; —$R^8SR^6$; nil; hydrogen; unsubstituted or substituted $C_1$–$C_8$ alkyl; monocyclic or polycyclic carbocyclic ring moiety; unsubstituted or substituted aryl; substituted or unsubstituted thiophene; substituted or unsubstituted oxathiazole; substituted or unsubstituted pyranones; substituted or unsubstituted furans; hydroxy; —$CO_2R^3$; —$O_2CR^3$; —$NR^3_2$; —$OR^3$; —$C(O)N(R^3)_2$; —$N(R^3)C(O)R^3$; substituted or unsubstituted benzyl; nitro; or combinations thereof;

(f) $R^2$ is independently selected from —$SR^6$, —$R^8SR^6$, —$CO_2R^3$; —$O_2CR^3$; —$C(O)N(R^3)_2$; —$N(R)^3C(O)R^3$; and nil; hydrogen; unsubstituted or substituted $C_1$–$C_8$ alkyl; unsubstituted or substituted aryl; hydroxy; substituted or unsubstituted benzyl; nitro; or combinations thereof;

(g) each $R^3$ is independently selected from hydrogen; substituted or unsubstituted $C_1$–$C_8$ alkyl; or $R^8SR^6$;

(h) $R^5$ is selected from —$SR^6$, $R^8SR^6$, hydrogen; hydroxy; amino; halogen; unsubstituted or substituted $C_1$–$C_8$ alkyl;

(i) $R^6$ is independently selected from H; —$C(O)R^7$; and $C(O)NR^7_2$; wherein $R^7$ is hydrogen; or unsubstituted or substituted $C_1$–$C_8$ alkyl; and (j) $R^8$ is a substituted or unsubstituted $C_1$–$C_8$ alkyl.

In this general structure, Z is a covalent bond, a monocyclic or polycyclic, saturated or unsaturated, substituted or unsubstituted, carbocyclic ring moiety, or a monocyclic or polycyclic, saturated or unsaturated, substituted or unsubstituted, heterocyclic ring moiety. In addition, m and n and m+n are integers from about 0 to about 10, n is preferably 1 to 5 and m+n is preferably 1 to 10. Q is a covalent bond or a moiety selected from the group consisting of oxygen or sulfur; R is $COOH$, $SO_3H$, $PO_3H_2$, or $P(O)(OH)R^4$. Further, in this general structure, each $R^1$, $R^2$, $R^3$ and $R^5$ is independently selected from a variety of substituent groups; most preferred $R^1$, $R^2$, $R^3$ and $R^5$ are alkoxy, hydrogen, hydroxy and amino. Most preferred $R^4$ is a $C_1$–$C_8$ alkyl and most preferred $R^5$ is hydrogen, halogen, amino or hydroxy. $R^6$ is most preferably H, $C(O)R^7$, or $C(O)NR^7_2$, wherein $R^7$ is hydrogen, or $C_1$–$C_8$ alkyl. Finally, in this general structure, when Q is S or O, the Q-containing chain is not attached to a Z heterocycle ring moiety at the heteroatom of a heterocycle ring.

The present invention further relates to novel thio-substituted compounds, their pharmaceutically-acceptable salts and esters, and to pharmaceutical compositions containing a safe and effective amount of said novel compounds, along with pharmaceutically-acceptable excipients. Finally, the present invention relates to methods for treating or preventing pathological conditions characterized by abnormal calcium and phosphate metabolism in humans or other mammals, particularly in treating arthritis. This method comprises administering to said human or other mammal in need of such treatment a safe and effective amount of a compound or composition of the present invention.

Novel thio-substituted compounds of the present invention have the following structure:

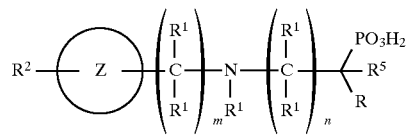

wherein m and n are integers 0 to 10 and m+n equals 0 to 10, and wherein (a) Z is a covalent bond; a monocyclic or polycyclic carbocyclic ring moiety; or a monocyclic or polycyclic heterocyclic ring moiety containing one or more heteroatoms selected from O, S, or N;

(b) R is $COOH$, $SO_3H$, $PO_3H_2$ or $P(O)(OH)R^4$, wherein $R^4$ is a substituted or unsubstituted $C_1$–$C_8$ alkyl;

(c) each $R^1$ is independently selected from —$SR^6$; —$R^8SR^6$; nil; hydrogen; unsubstituted or substituted $C_1$–$C_8$ alkyl; a monocyclic or polycyclic carbocyclic ring moiety; unsubstituted or substituted aryl; substituted or unsubstituted thiophene; substituted or unsubstituted oxathiazole; substituted or unsubstituted pyranones; substituted or unsubstituted furans; hydroxy; —$CO_2R^3$; —$O_2CR^3$; —$NR^3_2$; —$OR^3$; —$N(R^3)C(O)R^3$; —$C(O)N(R^3)_2$; substituted or unsubstituted benzyl; nitro; or combinations thereof;

(d) $R^2$ is independently selected from —$SR^6$, —$R^8SR^6$; —$CO_2R^3$; —$O_2CR^3$; —$NR^3_2$; —$N(R)^3C(O)R^3$, —$OR^3$; —$C(O)N(R^3)_2$; nil; hydrogen; unsubstituted or substituted $C_1$–$C_8$ alkyl; unsubstituted or substituted aryl; hydroxy; substituted or unsubstituted benzyl; nitro; or combinations thereof;

(e) each $R^3$ is independently selected from hydrogen; substituted or unsubstituted $C_1$–$C_8$ alkyl; or $R^8SR^6$;

(f) $R^5$ is selected from —$SR^6$; $R^8SR^6$; hydrogen; hydroxy; halogen; unsubstituted or substituted $C_1$–$C_8$ alkyl;

(g) $R^6$ is H, —$C(O)R^7$; $C(S)R^7$; $C(O)N(R^7)_2$; $C(S)N(R^7)_2$, $C(O)OR^7$ or $C(S)OR^7$; where $R^7$ is hydrogen, or unsubstituted or substituted $C_1$–$C_8$ alkyl; and (h) $R^8$ is substituted or unsubstituted $C_1$–$C_8$ alkyl; provided that at least one of R; $R^2$, $R^3$, or $R^5$ is $SR^6$ or $R^8SR^6$.

As stated above, it is essential that at least one of $R^1$, $R^2$, $R^3$ and $R^5$ is $SR^6$ or $R^8SR^6$; when any of $R^1$, $R^2$, $R^3$, or $R^5$ is $SR^6$ or $R^8SR^6$, the heterocyclic phosphonate is thio-substituted. Suitable thio-substituents in the compounds of the present invention are thiols, alkyl thiols, thioesters, alkyl thioesters, dithioesters, alkyl dithioesters, thiocarbamate, alkyl thiocarbamate, dithiocarbamate, alkyl dithiocarbamate, thiocarbonate, alkyl thiocarbonate, dithiocarbonate, and alkyl dithiocarbonates.

Finally, the present invention relates to the treatment of arthritis in humans or other mammals in need of such treatment comprising administering to said human or other mammal a safe and effective amount of a thio-substituted phosphonate compound having the following structure:

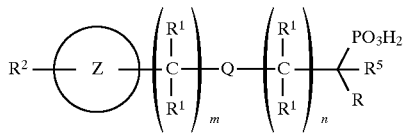

wherein m and n are integers 0 to 10 and m+n equals 0 to 10, and wherein (a) Z is a covalent bond, a monocyclic or polycyclic carbocyclic ring moiety; or a monocyclic or polycyclic heterocyclic ring moiety containing one or more heteroatoms selected from O, S, or N;

(b) Q is covalent bond, S or O, (c) R is COOH, $SO_3H$, $PO_3H_2$ or $P(O)(OH)R^4$, wherein $R^4$ is a substituted or unsubstituted $C_1$–$C_8$ alkyl;

(d) each $R^1$ is independently selected from —$SR^6$; —$R^8SR^6$; nil; hydrogen; unsubstituted or substituted $C_1$–$C_8$ alkyl; monocyclic or polycyclic carbocyclic ring moiety; unsubstituted or substituted aryl; substituted or unsubstituted thiophene; substituted or unsubstituted oxathiazole; substituted or unsubstituted pyranone; substituted or unsubstituted furan; hydroxy; —$CO_2R^3$; —$O_2CR^3$; —$NR^3{}_2$; —$OR^3$; —$N(R^3)C(O)R^3$; —$C(O)N(R^3)_2$; substituted or unsubstituted benzyl; nitro; or combinations thereof;

(e) $R^2$ is one or more substituents selected from —$SR^6$; —$R^8SR^6$; —$CO_2R^3$; —$OR^3$; —$O_2CR^3$; —$C(O)N(R^3)_2$; —$NR^3{}_2$; —$N(R)^3C(O)R^3$; and nil; hydrogen, substituted or unsubstituted $C_1$–$C_8$ alkyl; substituted or unsubstituted aryl; hydroxy; substituted or unsubstituted benzyl; nitro; or combinations thereof;

(f) each $R^3$ is independently selected from hydrogen; substituted or unsubstituted $C_1$–$C_8$ alkyl; or $R^8SR^6$;

(g) $R^5$ is selected from —$SR^6$; $R^8SR^6$; hydrogen; hydroxy; amino; halogen; unsubstituted or substituted $C_1$–$C_8$ alkyl;

(h) $R^6$ is H, —$C(O)R^7$; $C(S)R^7$; $C(O)N(R^7)_2$; $C(S)N(R^7)_2$, $C(O)OR^7$ or $C(S)OR^7$; where $R^7$ is hydrogen, or unsubstituted or substituted $C_1$–$C_8$ alkyl; and (i) $R^8$ is substituted or unsubstituted $C_1$–$C_8$ alkyl; and at least one of $R^1$, $R^2$, $R^3$ or $R^5$ must be $SR^6$ or $R^8SR^6$.

Said compounds are useful in the treatment of arthritis, especially rheumatoid arthritis and osteoarthritis, because they have osteoprotective activity at the site of joint destruction; this activity is an additional benefit over and above merely relieving the symptoms of inflammation.

DEFINITIONS AND USAGE OF TERMS

The following is a list of definitions for terms used herein.
"Heteroatom" is a nitrogen, sulfur, or oxygen atom. Groups containing one or more heteroatoms may contain different heteroatoms.

"Alkyl" is an unsubstituted or substituted, straight-chain or branched, saturated or unsaturated hydrocarbon chain, said hydrocarbon chain may be saturated, having 1 to 8 carbon atoms, and preferably, unless otherwise stated, from 1 to 4 carbon atoms; said hydrocarbon chain may be unsaturated, having 2 to 8 carbon atoms, and preferably, unless otherwise stated, 2 to 4 carbon atoms. Accordingly, the term "alkyl", as used herein, encompasses alkenyl hydrocarbon unsaturated chains having at least one olefinic double bond and alkynyl hydrocarbon unsaturated chains having at least one triple bond. Preferred alkyl groups include, but are not limited to, methyl, ethyl, propyl, isopropyl, and butyl.

"Heteroalkyl" is an unsubstituted or substituted, saturated chain having from 3 to 8-members and comprising carbon atoms and one or two heteroatoms.

"Carbocyclic ring" or "Carbocycle" as used herein is an unsubstituted or substituted, saturated or unsaturated or aromatic, hydrocarbon ring, generally containing from 3 to 8 atoms, preferably from 5 to 7, atoms. The term "carbocyclic ring moiety" as used herein encompasses monocyclic or polycyclic ring systems, fused or unfused, saturated or unsaturated, substituted or unsubstituted. Monocyclic carbocyclic ring moieties generally contain from 3 to 8, preferably from 5 to 7, carbon atoms, or they may be polycyclic. Polycyclic carbocyclic ring moieties consisting of two rings generally have from 6 to 16, preferably from 10 to 12, atoms. Polycyclic carbocycles consisting of three rings generally contain from 13 to 17, preferably from 14 to 15, atoms.

"Heterocyclic ring" or "heterocycle" as used herein is an unsubstituted or substituted, saturated, unsaturated or aromatic ring comprised of 3 to 8, preferably 5–7 carbon atoms, and one or more additional heteroatoms in the ring. The term "heterocyclic ring moiety" as used herein encompasses monocyclic or polycyclic ring systems, fused or unfused, unsaturated or saturated, substituted or unsubstituted. Monocyclic heterocyclic ring moieties generally contain from 3 to 8 atoms, preferably from 5 to 7, atoms. Polycyclic heterocyclic ring moieties consisting of two rings generally contain from 6 to 16, preferably from 10 to 12, atoms. Polycyclic heterocyclic ring moieties consisting of three rings generally contain from 13 to 17 atoms, preferably from 14 to 15, atoms. In addition, a polycyclic heterocyclic ring moiety may consist solely of heterocycles or of both heterocycles and carbocycles. Unless otherwise stated, the heteroatoms in the heterocyclic ring moiety may be independently chosen from nitrogen, sulfur, and oxygen.

"Aryl" is an aromatic carbocyclic ring. Preferred aryl groups include, but are not limited to, phenyl, tolyl, xylyl, cumenyl, and naphthyl.

"Heteroaryl" is an aromatic heterocyclic ring. Preferred heteroaryl groups include, but are not limited to, thienyl, furyl, pyrrolyl, pyridinyl, pyrazinyl, oxazolyl, thiazolyl, quinolinyl, pyrimidinyl, and tetrazolyl.

"Alkoxy" is an oxygen atom having a hydrocarbon chain substituent, where the hydrocarbon chain is an alkyl or alkenyl (e.g., —O-alkyl or —O-alkenyl). Preferred alkoxy groups include, but are not limited to, methoxy, ethoxy, propoxy, and alkyloxy.

"Hydroxyalkyl" is a substituted hydrocarbon chain which has a hydroxy substituent (e.g., —OH), and may have other substituents. Preferred hydroxyalkyl groups include, but are not limited to, hydroxyethyl, hydroxypropyl, and hydroxyalkyl.

"Carboxyalkyl" is a substituted hydrocarbon chain which has a carboxy substituent (e.g. —COOH) and may have other substituents. Preferred carboxyalkyl groups include carboxymethyl, carboxyethyl, and their acids and esters.

"Aminoalkyl" is a hydrocarbon chain (e.g. alkyl) substituted with an amine moiety (e.g., alkyl-NH-) such as aminomethyl.

"Alkylamino" is an amino moiety having one or two alkyl substituents (e.g., —N-alkyl), such as dimethylamine.

"Alkenylamino" is an amino moiety having one or two alkenyl substituents (e.g., —N-alkenyl).

"Alkynalamino" is an amino moiety having one or two alkynyl substituents (e.g., —N-alkynyl).

"Alkylimino" is an imino moiety having one or two alkyl substituents (e.g., —N-alkyl-).

"Arylalkyl" is an alkyl moiety substituted with an aryl group. Preferred arylalkyl groups include benzyl and phenylethyl.

"Arylamino" is an amine moiety substituted with an aryl group (e.g., —NH-aryl).

"Aryloxy" is an oxygen atom having an aryl substituent (e.g., —O-aryl).

"Acyl" or "carbonyl" is a carbon to oxygen double bond, (e.g., R—C(=O)-). Preferred alkylacyl groups include, but are not limited to, acetyl, propionyl, butanoyl and benzoyl.

"Acyloxy" is an oxygen atom having an acyl substituent (e.g., —O-acyl); for example, —O—C(=O)-alkyl.

"Acylamino" is an amino moiety having an acyl substituent (e.g., —N-acyl); for example, —NH—(C=O)-alkyl.

"Halo", "halogen", or "halide" is a chloro, bromo, fluoro, or iodo atom radical. Chloro, bromo, and fluoro are preferred halides.

Also, as referred to herein, a "lower" hydrocarbon moiety (e.g., "lower" alkyl) is a hydrocarbon chain comprised of from, unless otherwise stated, 1 to 6, preferably from 1 to 4, carbon atoms.

As used herein, the term "thio-substituent" is depicted by $SR^6$ or $R^8SR^6$, wherein $R^8$ is a $C_1$–$C_8$ alkyl. Particular thio-substituents include thiol (—SH, where $R^6$=H); thioesters

where $R^6$ is $COR^7$); thiocarbamates

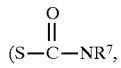

where $R^6$ is $CONR^7$); dithiocarbamates

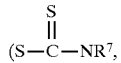

where $R^6$ is $CSNR^7_2$); dithioesters

where $R^6$ is $CSR^7$, thiocarbonates

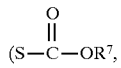

where $R^6$ is $C(O)OR^7$), and dithiocarbonates

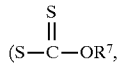

where $R^6$ is $C(S)OR^7$). $R^7$ as used herein is hydrogen or substituted or unsubstituted $C_1$–$C_8$ alkyl. It is to be understood that the $SR^6$ groups defined above can be preceded by an $R^8$ (i.e. a $C_1$–$C_8$ alkyl); this would yield alkyl thiols, alkyl thioesters, alkyl dithioesters, alkyl thiocarbamates, alkyl dithiocarbamates, alkyl thiocarbonates and alkyl dithiocarbonates.

The terms "bisphosphonate" or "bisphosphonic acid" as used herein relate to those phosphonate or phosphonic acids that have two phosphonate groups attached to the same carbon atom and are used interchangeably with the terms diphosphonate and diphosphonic acids. Using the structures described herein, in these compounds the moiety R is $PO_3H_2$.

A "pharmaceutically-acceptable" salt is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987, hereby incorporated by reference herein. Preferred cationic salts include the alkali-metal salts (such as sodium and potassium), and alkaline earth metal salts (such as magnesium and calcium). Preferred anionic salts include the halide (such as chloride), acetates and phosphate salts.

A "biohydrolyzable ester" is an ester of phosphonate compounds that does not interfere with the activity of the compounds, or that is readily metabolized by a human or other mammal to yield an active compound. Many such esters are known in the art, as described in World Patent Publication 87/05297, Johnston et al., published Sep. 11, 1987, and hereby incorporated by reference herein. Such esters include lower alkyl esters, lower acyloxyalkyl esters (such as acetoxymethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters).

As defined above and as used herein, substituent groups may themselves be substituted. Such substitution may be with one or more substituents. Such substituents include, but are not limited to, those listed in C. Hansch and A. Leo, *Substituent Constants for Correlation Analysis in Chemistry and Biology* (1979), hereby incorporated by reference herein. Preferred substituents include, but are not limited to, alkyl, alkenyl, alkoxy, hydroxy, oxo, amino, aminoalkyl (e.g. aminomethyl, etc.), cyano, halo, carboxy, alkoxyacetyl (e.g. carboethoxy, etc.), thio, thiol, aryl, cycloalkyl, heteroaryl, heterocycloalkyl (e.g., piperidinyl, morpholinyl, piperazinyl, pyrrolidinyl, etc.), imino, thioxo, hydroxyalkyl, aryloxy, arylalkyl, and combinations thereof.

DETAILED DESCRIPTION OF THE INVENTION

Novel Sulfur-containing Phosphonate Compounds

The novel sulfur-containing phosphonic acid compounds of the present invention, and the pharmaceutically-acceptable salts and esters thereof, are linked through a sulfur-containing linking chain; the phosphonic acid-containing carbon atom is linked to a sulfur-containing chain, which also contains a carbonyl carbon atom. The moiety Z may be a covalent bond, a carbocyclic ring moiety, or a heterocyclic ring moiety. The linkage from the phosphonic acid containing-carbon atom to the sulfur atom may be direct through a covalent bond (preferably a single bond), or by a chain of length (n) of from about 1 to about 10 atoms.

The carbon atoms in the linking chain and in the sulfur-containing chain may, independently, be unsubstituted or substituted with one or more substituents selected from thio-substituents (including thiols, alkyl thiols, thioesters, alkyl thioesters, thiocarbamates, and alkyl thiocarbamates), hydrogen, alkoxy, hydroxy, methyl, ethyl, or propyl.

For the compounds in which an oxygen atom is bonded to a heterocycle ring moiety (Z), this oxygen atom is bonded to the ring at a carbon atom and not bonded directly to the ring's heteroatom. When Q is a covalent bond, then the linking chain may be bonded to either a carbon atom or a heteroatom in the ring (Z).

The carbon atom which has the phosphonate group attached to it may be unsubstituted (i.e., a hydrogen atom), or substituted. The carbon atom may be substituted with two phosphonate groups (rendering a bisphosphonate compound); or with one phosphonate group and one phosphinate group (yielding a phosphonoalkylphosphinate compound); a phosphonate group and a sulfonate group (yielding a phosphonosulfonate compound); or a phosphonate group and a carboxylate group, (yielding a phosphonocarboxylate compound).

Furthermore, the carbon atoms in the heterocycle ring (Z) may be unsubstituted or substituted independently with one or more substituents. The heteroatoms in the heterocycle ring may be unsubstituted or substituted.

Thus, the sulfur-containing phosphonic acids of the present invention, and the pharmaceutically-acceptable salts and esters thereof, have the general structure:

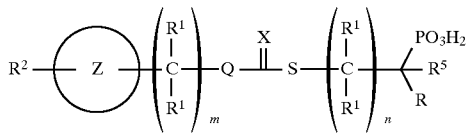

wherein m and n are integers 0 to 10 and m+n equals 0 to 10, and wherein (a) X is O or S;

(b) Z is a covalent bond; a monocyclic or polycyclic carbocycle ring moiety; or a monocyclic or polycyclic heterocyclic ring moiety containing one or more heteroatoms selected from O, S, or N;

(c) Q is covalent bond; O; or S;

(d) R is COOH, $SO_3H$, $PO_3H_2$, or $P(O)(OH)R^4$, wherein $R^4$ is substituted or unsubstituted $C_1$–$C_8$ alkyl;

(e) each $R^1$ is independently selected from —$SR^6$; —$R^8SR^6$; nil; hydrogen; unsubstituted or substituted $C_1$–$C_8$ alkyl; monocyclic or polycyclic carbocyclic ring moiety; unsubstituted or substituted aryl; substituted or unsubstituted thiophene; substituted or unsubstituted oxathiazole; substituted or unsubstituted pyranones; substituted or unsubstituted furans; hydroxy;—$CO_2R^3$; —$O_2CR^3$; —$NR^3_2$; —$OR^3$; —$C(O)N(R^3)_2$; —$N(R^3)C(O)R^3$; substituted or unsubstituted benzyl; nitro; or combinations thereof;

(f) $R^2$ is independently selected from —$SR^6$, —$R^8SR^6$, —$CO_2R^3$; —$O_2CR^3$; —$C(O)N(R^3)_2$; —$N(R)^3C(O)R^3$; and nil; hydrogen; unsubstituted or substituted $C_1$–$C_8$ alkyl; unsubstituted or substituted aryl; hydroxy; substituted or unsubstituted benzyl; nitro; or combinations thereof;

(g) each $R^3$ is independently selected from hydrogen; substituted or unsubstituted $C_1$–$C_8$ alkyl; or $R^8SR^6$;

(h) $R^5$ is selected from —$SR^6$, $R^8SR^6$, hydrogen; hydroxy; amino; halogen; substituted or unsubstituted $C_1$–$C_8$ alkyl; and (i) $R^6$ is independently selected from H; —$C(O)R^7$; and $C(O)NR^7_2$; wherein $R^7$ is hydrogen; or unsubstituted or substituted $C_1$–$C_8$ alkyl; and (j) $R^8$ is a substituted or unsubstituted $C_1$–$C_8$ alkyl.

In this general structure, Z is a covalent bond; a monocyclic or polycyclic, saturated or unsaturated, substituted or unsubstituted, carbocyclic ring moiety; or a monocyclic or polycyclic, saturated or unsaturated, substituted or unsubstituted, heterocyclic ring moiety. Said heterocyclic ring moiety may be a monocyclic ring system (i.e., one heterocyclic ring) or may be polycyclic ring system (i.e., one heterocyclic ring, and one or more heterocycle or carbocyclic rings). Each Z moiety may contain one or more heteroatoms selected from oxygen, sulfur or nitrogen.

In these general structures, Q is a covalent bond, (preferably a single bond), sulfur or oxygen. Further, m and n and m+n are integers from about 0 to about 10, with n equals 1 to 5 and m+n equals 1 to 10 being preferred.

The R moieties described herein may be COOH, $SO_3H$, $PO_3H_2$ or $P(O)(OH)R^4$, wherein $R^4$ is $C_1$–$C_8$ alkyl. When R is $PO_3H_2$, the thio-substituted phosphonate compound is a bisphosphonate; when R is $P(O)(OH)R^4$, the thio-substituted phosphonate compound is a phosphonoalkylphosphinate, when R is $SO_3H$, the thio-substituted phosphonate compound is a phosphonosulfonate; when R is COOH, the thio-substituted phosphonate compound is a phosphonocarboxylate.

The $R^1$ moieties are substituents and are independently selected from thiol, alkyl thiol, thioesters, alkyl thioesters, thiocarbamate, alkyl thiocarbamate, hydrogen, halogen, $C_1$–$C_8$ alkyl, unsubstituted or substituted aryl, unsubstituted or substituted benzyl; hydroxy; —$C(O)N(R^3)_2$; —$OR^3$; —$CO_2R^3$; —$O_2CR^3$; $NR^3_2$; —$N(R^3)C(O)R^3$; nitro; and combinations thereof; wherein $R^3$ is independently selected from $R^8SR^6$, hydrogen, or substituted or unsubstituted $C_1$–$C_8$ alkyl, preferably hydrogen or $C_1$–$C_8$ alkyl. When Q is a covalent bond and any $R^1$ is nil, an adjacent $R^1$ must be nil; this indicates an unsaturated chain. However, when n=0, then $R^5$ is selected from hydrogen; $R^8SR^6$; and alkyl having from about 1 to about 6 carbon atoms.

Preferred $R^1$ is selected from hydrogen, chloro, methyl, ethyl, hydroxy, unsubstituted amino, (N-methyl)amino, (N,N-dimethyl)amino, —$CO_2H$ and the pharmaceutically-acceptable salts thereof, —$CO_2CH_3$ and —$CONH_2$. More preferred $R^1$ is selected from hydrogen, methyl, chloro, amino, and hydroxy. Most preferred $R^1$ is hydrogen, hydroxy, or amino.

The Z moiety (when it is a carbocyclic ring moiety or a heterocyclic ring moiety) in the compounds of the present invention may be unsubstituted or substituted on the atoms of the ring independently with one or more substituents ($R^2$). The $R^2$ groups may be on the same carbon atom, or on different atoms of the Z moiety.

Thus, the $R^2$ groups are substituents, on one or more atoms of the heterocycle, and are independently selected from nil; $SR^6$; $R^8SR^6$; hydrogen; halogen; $C_1$–$C_8$ alkyl; unsubstituted or substituted aryl; unsubstituted or substituted benzyl; —$C(O)N(R^3)_2$, —$OR^3$; —$CO_2R^3$; —$O_2CR^3$; —$NR^3_2$; —$N(R^3)C(O)R^3$; nitro, and combinations thereof, wherein $R^3$ is independently selected from hydrogen, or unsubstituted or substituted $C_1$–$C_8$ alkyl, preferably hydrogen.

Preferred $R^2$ substituents are independently selected from thio-substituents; ($SR^6$, $R^8SR^6$), hydrogen, methyl, ethyl, hydroxy unsubstituted amino, (N-methyl)amino, (N,N-dimethyl)amino, chloro, methoxy, ethoxy, nitro, —$CO_2H$ and the pharmaceutically-acceptable salts thereof, —$CO_2CH_3$, $CONH_2$, and combinations thereof. More preferred $R^2$ substituents are independently selected from hydrogen, methyl, amino, chloro, methoxy, hydroxy and combinations thereof. Most preferred $R^2$ substituents are independently selected from amino, hydrogen and methyl.

$R^5$ in the general structure hereinabove denotes hydrogen, halogen, hydroxy, amino, thio-substituents, i.e. $SR^6$ or $R^8SR^6$, unsubstituted or substituted $C_1$–$C_8$ alkyl. Preferred $R^5$ is hydroxy, amino, hydrogen, halogen, thio; most preferred $R^5$ is hydroxy, amino, and hydrogen.

$R^6$ denotes a substituent on the sulfur-containing substituent, —$SR^6$. $R^6$ is hydrogen; —$C(O)R^7$; —$C(O)NR^7{}_2$; wherein $R^7$ is hydrogen, or unsubstituted or substituted $C_1$–$C_8$ alkyl. Preferred $R^6$ is H, $C(O)R^7$, $C(O)NR^7$; most preferred $R^6$ is hydrogen. Preferred $R^7$ is hydrogen or $C_1$–$C_8$ alkyl.

The Z moiety of the compounds of the present invention is a covalent bond, a carbocyclic ring moiety, or a heterocyclic ring moiety. Said heterocyclic ring moiety has one or more heteroatoms selected from O, S, or N. The Z moiety may be a monocyclic carbocyclic or heterocyclic ring moiety having from 3 to 8 atoms, or may be a polycyclic carbocyclic or heterocyclic ring moiety having 6 to 17 atoms. Said polycyclic ring moiety may contain two or more carbocycles, two or more heterocycles, or one or more heterocycle along with one or more carbocyclic rings.

Preferred monocyclic Z moieties which are heterocyclic ring moieties are pyrimidine, pyrazine, piperidine, and pyridine. Preferred polycyclic Z moieties which are heterocyclic ring moieties are quinolines, pyrrolopyridines, quinoxalines and imidazopyridines. Preferred monocyclic Z moieties which are carbocyclic ring moieties are phenyl, cyclopentyl, cyclohexyl, and cycloheptyl.

Furthermore in the hereinbefore general structures, when m=0 and Q is oxygen, then the bonding of the Q moiety to a heterocyclic ring moiety (Z) is preferably limited as follows. The Q moiety is bonded to the heterocycle ring at a carbon atom and not bonded directly to a heteroatom in the heterocycle ring.

Preferred sulfur-containing phosphonate compounds having a carbonyl carbon in the chain which links the phosphorus-containing carbon atom to the Z moiety include, but are not limited to, thioesters, dithioesters, thiocarbonates, and dithiocarbonates. Preferred thioesters include compounds having the following general structures:

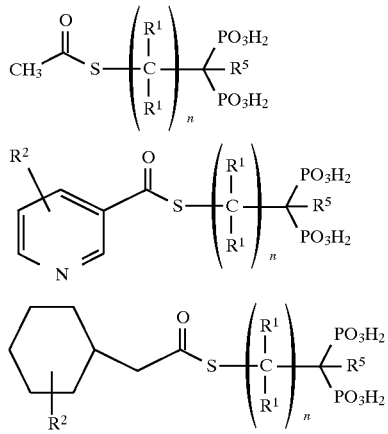

Preferred dithioesters include compounds having the following general structures:

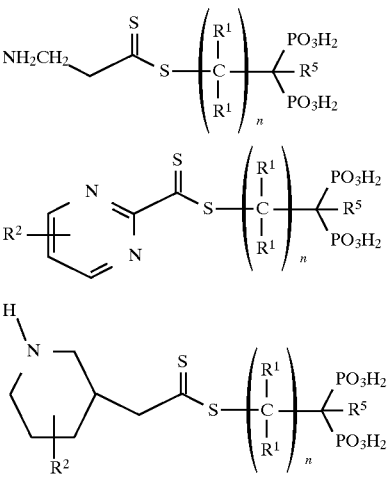

Preferred thiocarbonates include compounds which have the following general structures:

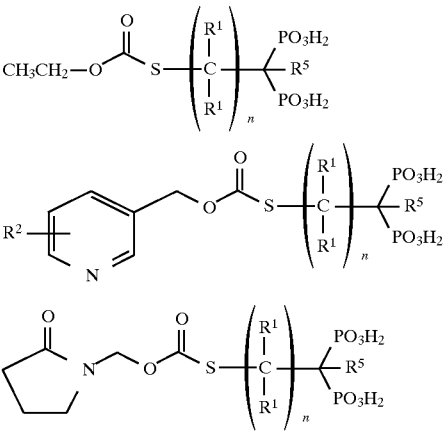

Preferred dithiocarbonates include compounds which have the following general structure:

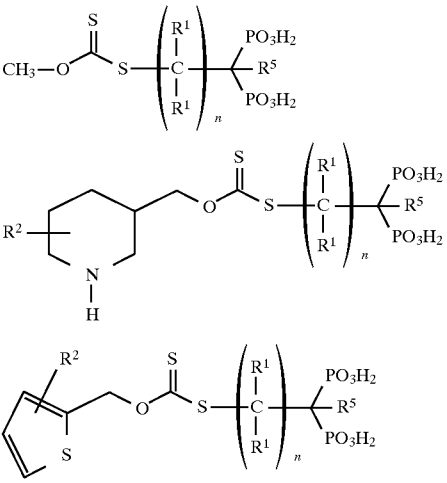

Novel thio-substituted compounds

The present invention further relates to novel thio-substituted compounds, their pharmaceutically-acceptable salts and esters, and to pharmaceutical compositions containing a safe and effective amount of said novel compounds, and pharmaceutically-acceptable excipients. In addition, the present invention relates to methods for treating or preventing pathological conditions characterized by abnormal calcium and phosphate metabolism in humans or other mammals. This method comprises administering to said human or other mammal in need of such treatment a safe and effective amount of a compound or composition of the present invention. These novel thio-substituted compounds have the following general structure:

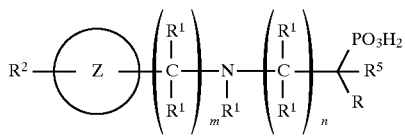

wherein m and n are integers from 0 to 10 and m+n equals 0 to 10 and wherein (a) Z is a covalent bond; a monocyclic or polycyclic carbocyclic ring moiety; or a monocyclic or polycyclic heterocyclic ring moiety containing one or more heteroatoms selected from O, S, or N;

(b) R is COOH; $SO_3H$; $PO_3H_2$ or $P(O)(OH)R^4$; wherein $R^4$ is $C_1$–$C_8$ alkyl;

(c) each $R^1$ is independently selected from —$SR^6$; —$R^8SR^6$; nil; hydrogen; unsubstituted or substituted $C_1$–$C_8$ alkyl; a monocyclic or polycyclic carbocyclic ring moiety; unsubstituted or substituted aryl; substituted or unsubstituted thiophene; substituted or unsubstituted oxathiazole; substituted or unsubstituted pyranones; substituted or unsubstituted furans; hydroxy; —$CO_2R^3$; —$O_2CR^3$; —$NR^3_2$; —$N(R^3)C(O)R^3$; —$OR^3$; —$C(O)N(R^3)_2$; substituted or unsubstituted benzyl; nitro; or combinations thereof;

(d) $R^2$ is independently selected from —$SR^6$; —$R^8SR^6$; —$CO_2R^3$; —$O_2CR^3$; —$NR^3_2$; —$N(R)^3C(O)R^3$; $OR^3$; —$C(O)N(R^3)_2$; nil; hydrogen; unsubstituted or substituted $C_1$–$C_8$ alkyl; unsubstituted or substituted aryl; hydroxy; substituted or unsubstituted benzyl; nitro; or combinations thereof;

(e) each $R^3$ is independently selected from hydrogen; substituted or unsubstituted $C_1$–$C_8$ alkyl; or $R^8SR^6$;

(f) $R^5$ is selected from —$SR^6$; $R^8SR^6$; hydrogen; hydroxy; unsubstituted or substituted $C_1$–$C_8$ alkyl; amino; halogen;

(g) $R^6$ is H; —$C(O)R^7$; —$C(S)R^7$; —$C(O)NR^7_2$; —$C(S)NR^7_2$; $C(O)OR^7$; or $C(S)OR^7$, wherein $R^7$ is hydrogen, or unsubstituted or substituted $C_1$–$C_8$ alkyl; and (i) $R^8$ is $C_1$–$C_8$ substituted or unsubstituted alkyl; and at least one of $R^1$, $R^2$, $R^3$ or $R^5$ is $SR^6$ or $R^8SR^6$.

In this general structure, Z is a covalent bond; a saturated or unsaturated, substituted or unsubstituted, carbocyclic ring moiety; a monocyclic or polycyclic, saturated or unsaturated, substituted or unsubstituted, heterocyclic ring moiety. Said Z moiety may be a monocyclic ring system (i.e., one carbocyclic ring or one heterocyclic ring) or may be a polycyclic ring system (i.e., one or more heterocyclic rings, one or more carbocyclic rings and one or more heterocycle along with one or more carbocyclic rings). Each Z moiety may contain one or more heteroatoms selected from oxygen, sulfur or nitrogen.

In these general structures, m and n and m+n are integers from about 0 to about 10, with n=1 to 5 and m+n=1 to 10 being preferred.

The R moieties described herein may be COOH, $SO_3H$, $PO_3H_2$ or $P(O)(OH)R^4$, wherein $R^4$ is $C_1$–$C_8$ alkyl. When R is $PO_3H_2$, the thio-substituted phosphonate compound is a bisphosphonate; when R is $P(O)(OH)R^4$, the thio-substituted phosphonate compound is a phosphonoalkylphosphinate, when R is $SO_3H$, the thio-substituted phosphonate compound is a phosphonosulfonate; when R is COOH, the thio-substituted phosphonate compound is a phosphonocarboxylate.

As stated above, it is essential that at least one of $R^1$, $R^2$, $R^3$ or $R^5$ is $SR^6$ or $R^8SR^6$; where any of $R^1$, $R^2$, $R^3$, and $R^5$ is $SR^6$ or $R^8SR^6$, the phosphonate compound is thio-substituted. Suitable thio-substituents for the compounds of the present invention include thiols, alkyl thiols, thioesters, alkyl thioesters, dithioesters, alkyl dithioesters, thiocarbamate, alkyl thiocarbamate, dithiocarbamate, alkyl dithiocarbamate, thiocarbonate, alkyl thiocarbonate, dithiocarbonate, and alkyl dithiocarbonate.

The $R^1$ moieties are substituents and are independently selected from thiol, alkyl thiol, thioesters, alkyl thioesters, dithioesters, alkyl dithioesters, thiocarbamate, alkyl thiocarbamate, dithiocarbamate, alkyl dithiocarbamate, thiocarbonates, alkyl thiocarbonates, dithiocarbonates, alkyl dithiocarbonates, hydrogen, halogen, $C_1$–$C_8$ alkyl, unsubstituted or substituted aryl, unsubstituted or substituted benzyl; hydroxy; —$C(O)N(R^3)_2$; —$OR^3$; —$CO_2R^3$; —$O_2CR^3$; $NR^3_2$; —$N(R^3)C(O)R^3$; nitro; and combinations thereof; wherein $R^3$ is independently selected from $R^8SR^6$, hydrogen, or substituted or unsubstituted $C_1$–$C_8$ alkyl, preferably thio-substituted alkyls.

However, when n=0, then $R^5$ is selected from hydrogen; $R^8SR^6$; alkyl having from about 1 to about 8 carbon atoms; the pharmaceutically-acceptable salts and esters thereof; and combinations thereof.

Preferred $R^1$ is selected from thio-substituents, hydrogen, chloro, methyl, ethyl, hydroxy, unsubstituted amino, (N-methyl)amino, (N, N-dimethyl)amino, —$CO_2H$ and the pharmaceutically-acceptable salts thereof, —$CO_2CH_3$ and —$CONH_2$. More preferred $R^1$ is selected from thiol, (or thio-containing substituents), hydrogen, methyl, chloro, amino, and hydroxy. Most preferred $R^1$ is thiol, hydrogen, hydroxy, or amino. In addition, as stated hereinabove, it is essential that the compounds of the present invention, at least one of $R^1$, $R^2$, $R^3$ and $R^5$ be a thio-containing substituent, i.e. $SR^6$ or $R^8SR^6$.

When the Z moiety is a carbocyclic ring moiety or a heterocyclic ring moiety, said ring moiety may be unsubstituted or substituted on the atoms of the ring independently with one or more substituents ($R^2$). The $R^2$ groups may be on the same carbon atom, or on different atoms of the ring moiety.

Thus, the $R^2$ groups are substituents, on one or more atoms of the heterocycle, and are independently selected from nil; $SR^6$; $R^8SR^6$; hydrogen; halogen; $C_1$–$C_8$ alkyl; unsubstituted or substituted aryl; unsubstituted or substituted benzyl; —$C(O)N(R^3)_2$; —$OR^3$; —$CO_2R^3$; —$O_2CR^3$; —$NR^3_2$; —$N(R^3)C(O)R^3$; nitro, and combinations thereof, wherein $R^3$ is independently selected from hydrogen, or unsubstituted or substituted $C_1$–$C_8$ alkyl, preferably thio-substituted alkyl.

Preferred $R^2$ substituents are independently selected from thio-substituents; ($SR^6$, $R^8SR^6$), hydrogen, methyl, ethyl, hydroxy unsubstituted amino, (N-methyl)amino, (N,N-dimethyl)amino, chloro, methoxy, ethoxy, nitro, —$CO_2H$ and the pharmaceutically-acceptable salts thereof, —$CO_2CH_3$, $CONH_2$, and combinations thereof. More preferred $R^2$ substituents are independently selected from thio-containing substituents; hydrogen, methyl, amino, chloro, methoxy, hydroxy and combinations thereof. Most preferred $R^2$ substituents are independently selected from thio-containing substituents; hydrogen and methyl. In addition, as stated hereinabove, it is essential that in the compounds of the present invention, at least one of $R^1$, $R^2$, $R^3$ and $R^5$ be a thio-containing substituent, i.e. $SR^6$ or $R^8SR^6$.

$R^5$ in the general structure hereinabove denotes hydrogen, halogen, hydroxy, amino, thio-substituents, i.e. $SR^6$ or $R^8SR^6$, unsubstituted or substituted $C_1$–$C_8$ alkyl. Preferred $R^5$ is hydroxy, amino, hydrogen, halogen, thio; most preferred $R^5$ is hydroxy, amino, and hydrogen.

$R^6$ denotes a substituent on the sulfur-containing substituent, —$SR^6$. $R^6$ is hydrogen; —$C(O)R^7$; $C(S)R^7$; —$C(O)NR^7{}_2$; —$C(S)NR^7{}_2$; —$C(O)OR^7$, —$C(S)OR^7$, wherein $R^7$ is hydrogen, or unsubstituted or substituted $C_1$–$C_8$ alkyl. Preferred $R^6$ is H, $C(O)R^7$, $C(O)NR^7$; most preferred $R^6$ is hydrogen. Preferred $R^7$ is hydrogen or $C_1$–$C_8$ alkyl.

The Z moiety of the present invention is a covalent bond; a carbocyclic ring moiety or a heterocyclic ring moiety which has one or more heteroatoms selected from O, S, or N. The Z moiety may be a monocyclic carbocyclic ring moiety or a heterocyclic ring moiety having from 3 to 8 atoms or may be a polycyclic carbocyclic ring moiety or a heterocyclic ring moiety having 6 to 17 atoms. Said polycyclic ring moiety may contain two or more carbocycles, or two or more heterocycles, or one or more heterocycles along with one or more carbocyclic rings.

Preferred monocyclic Z moieties which are heterocyclic ring moieties are pyrimidine, pyrazine, piperidine, and pyridine. Preferred polycyclic Z moieties which are heterocyclic ring moieties are quinolines, pyrrolopyridines, quinoxalines and imidazopyridines. Preferred monocyclic Z moieties which are carbocyclic ring moieties are phenyl, cyclopentyl, cyclohexyl, and cycloheptyl.

Furthermore in the hereinbefore general structures, when m=0, then the bonding of the $NR^1$ moiety to a heterocyclic ring moiety (Z) is preferably limited as follows. The $NR^1$ moiety is bonded to the heterocycle ring at a carbon atom.

Preferred novel thio-substituted phosphonate compounds of the present invention include, but are not limited to, compounds having the following general structures:

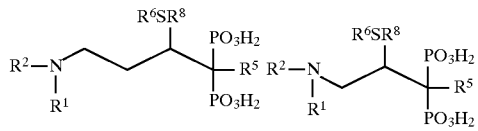

Especially preferred are the following thio-substituted aminoalkylidene bisphosphonate compounds:

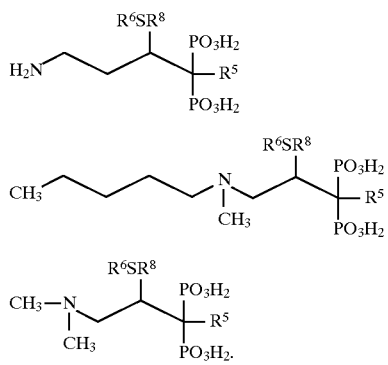

Thio-substituted compounds useful in the treatment of disorders of calcium and phosphate metabolism Finally, the present invention relates to the treatment of disorders of calcium and phosphate metabolism, particularly arthritis, especially rheumatoid arthritis and osteoarthritis, in humans or other mammals in need of such treatment. Said method comprises administering to said human or other mammal a safe and effective amount of thio-substituted phosphonate compound having the following structure:

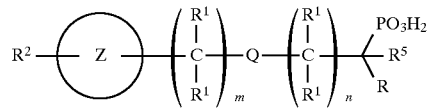

wherein m and n are integers from 0 to 10 and m+n equals 0 to 10, and wherein (a) Z is a covalent bond; a monocyclic or polycyclic carbocyclic ring moiety; or a monocyclic or polycyclic heterocyclic ring moiety containing one or more heteroatoms selected from O, S, or N;

(b) Q is covalent bond, S, O, N, or $NR^1$;

(c) R is COOH; $SO_3H$; $PO_3H_2$ or $P(O)(OH)R^4$; wherein $R^4$ is $C_1$–$C_8$ alkyl;

(d) each $R^1$ is independently selected from —$SR^6$; —$R^8SR^6$; nil; hydrogen; unsubstituted or substituted $C_1$–$C_8$ alkyl; substituted or unsubstituted monocyclic or polycyclic carbocycle; unsubstituted or substituted aryl; substituted or unsubstituted thiophene; substituted or unsubstituted oxathiazole; substituted or unsubstituted pyranone; substituted or unsubstituted furan; hydroxy; alkoxy; —$CO_2R^3$; —$O_2CR^3$; —$NR^3{}_2$; —$N(R^3)C(O)R^3$; —$OR^3$; —$C(O)N(R^3)_2$; substituted or unsubstituted benzyl; nitro; or combinations thereof;

(e) $R^1$ is one or more substituents selected from —$SR^6$; —$R^8SR^6$; —$CO_2R^3$; —$O_2CR^3$; —$C(O)N(R^3)_2$; —$NR^3{}_2$; —$N(R^3)C(O)R^3$; and nil; hydrogen; substituted or unsubstituted $C_1$–$C_8$ alkyl; substituted or unsubstituted aryl; hydroxy; substituted or unsubstituted benzyl; nitro; or combinations thereof;

(f) each $R^3$ is independently selected from hydrogen; substituted or unsubstituted $C_1$–$C_8$ alkyl; or $R^8SR^6$;

(g) $R^5$ is selected from —$SR^6$; $R^8SR^6$; hydrogen; hydroxy; unsubstituted or substituted $C_1$–$C_8$ alkyl; amino; halogen;

(h) $R^6$ is H; —$C(O)R^7$; —$C(S)R^7$; —$C(O)NR^7{}_2$; —$C(S)NR^7{}_2$; $C(O)OR^7$; or $C(S)OR^7$, wherein $R^7$ is hydrogen, or unsubstituted or substituted $C_1$–$C_8$ alkyl; and (i) $R^8$ is $C_1$–$C_8$ substituted or unsubstituted alkyl; and at least one of $R^1$, $R^2$, $R^3$ or $R^5$ is $SR^6$ or $R^8SR^6$.

These compounds are useful in the treatment of arthritis, and other disorders of calcium and phosphate metabolism; these compounds demonstrate osteoprotective activity at the site of joint destruction. This activity involves disease-modifying activity at the site of joint destruction, which is a benefit over and above merely relieving the symptoms of inflammation.

In these general structures, Q is a covalent bond, (preferably a single bond) or a moiety selected from oxygen, sulfur, nitrogen, or —$NR^1$—. Further, m and n and m+n are integers from about 0 to about 10, with m+n being 1 to 5 preferred.

The R moieties described herein may be COOH, $SO_3H$, $PO_3H_2$ or $P(O)(OH)R^4$, wherein $R^4$ is $C_1$–$C_8$ alkyl. When R is $PO_3H_2$, the thio-substituted phosphonate compound is a bisphosphonate; when R is $P(O)(OH)R^4$, the thio-substituted phosphonate compound is a phosphonoalkylphosphinate, when R is $SO_3H$, the thio-substituted phosphonate compound is a phosphonosulfonate; when R is COOH, the thio-substituted phosphonate compound is a phosphonocarboxylate.

As stated above, it is essential that at least one of $R^1$, $R^2$, $R^3$ or $R^5$ is $SR^6$ or $R^8SR^6$; where any of $R^1$, $R^2$, $R^3$ and $R^5$ is $SR^6$ or $R^8SR^6$, the phosphonate compound is thio-substituted. Suitable thio-substituents for the compounds of the present invention include thiols, alkyl thiols, thioesters, alkyl thioesters, dithioesters, alkyl dithioesters, thiocarbamate, alkyl thiocarbamate, dithiocarbamate, alkyl dithiocarbamate, thiocarbonate, alkyl thiocarbonate, dithiocarbonate, and alkyl dithiocarbonate.

The $R^1$ moieties are substituents and are independently selected from thiol, alkyl thiol, thioesters, alkyl thioesters, dithioesters, alkyl dithioesters, thiocarbamate, alkyl thiocarbamate, dithiocarbamate, alkyl dithiocarbamate, thiocarbonates, alkyl thiocarbonates, dithiocarbonates, alkyl dithiocarbonates, hydrogen, halogen, $C_1$–$C_8$ alkyl, unsubstituted or substituted aryl, unsubstituted or substituted benzyl; hydroxy; —C(O)N($R^3$)$_2$; —O$R^3$; —CO$_2R^3$; —O$_2$C$R^3$; N$R^3_2$; —N($R^3$)C(O)$R^3$; nitro; and combinations thereof; wherein $R^3$ is independently selected from $R^8SR^6$, hydrogen, or substituted or unsubstituted $C_1$–$C_8$ alkyl, preferably thio-substituted alkyls. When Q is a covalent bond and any $R^1$ is nil, an adjacent $R^1$ must be nil; this indicates an unsaturated chain. When Q is N$R^1$, $R^1$ may be nil to indicated a carbon to nitrogen double bond.

However, when n=0 and Q is oxygen, sulfur, or nitrogen, then $R^5$ is selected from hydrogen; $R^8SR^6$; alkyl having from about 1 to about 8 carbon atoms; the pharmaceutically-acceptable salts and esters thereof; and combinations thereof.

Preferred $R^1$ is selected from thio-substituents, hydrogen, chloro, methyl, ethyl, hydroxy, unsubstituted amino, (N-methyl)amino, (N, N-dimethyl)amino, —CO$_2$H and the pharmaceutically-acceptable salts thereof, —CO$_2$CH$_3$ and —CONH$_2$. More preferred $R^1$ is selected from thiol, (or thio-containing substituents), hydrogen, methyl, chloro, amino, and hydroxy. Most preferred $R^1$ is thiol, hydrogen, hydroxy, or amino. In addition, as stated hereinabove, it is essential that the compounds of the present invention, at least one of $R^1$, $R^2$, $R^3$ and $R^5$ be a thio-containing substituent, i.e. $SR^6$ or $R^8SR^6$.

$R^5$ in the general structure hereinabove denotes hydrogen, halogen, hydroxy, amino, thio-substituents, i.e. $SR^6$ or $R^8SR^6$, unsubstituted or substituted $C_1$–$C_8$ alkyl. Preferred $R^5$ is hydroxy, amino, hydrogen, halogen, thio; most preferred $R^5$ is hydroxy, amino, and hydrogen.

$R^6$ denotes a substituent on the sulfur-containing substituent, —S$R^6$. $R^6$ is hydrogen; —C(O)$R^7$; C(S)$R^7$; —C(O)N$R^7_2$; —C(S)N$R^7_2$; —C(O)O$R^7$, —C(S)O$R^7$, wherein $R^7$ is hydrogen, or unsubstituted or substituted $C_1$–$C_8$ alkyl. Preferred $R^6$ is H, C(O)$R^7$, C(O)N$R^7$; most preferred $R^6$ is hydrogen. Preferred $R^7$ is hydrogen or $C_1$–$C_8$ alkyl.

Furthermore in the hereinbefore general structures, when m=0 and Q is oxygen, sulfur, or nitrogen, then the bonding of the Q moiety to the heterocycle ring is preferably limited as follows. The Q moiety is bonded to the heterocycle ring at a carbon atom.

Specific examples of compounds of the present invention include:

[2-[(2,2-dimethyl-1-oxopropyl)thio]ethylidene]bis [phosphonic acid];
[2-(benzoylthio)ethylidene]bis[phosphonic acid];
[2-(p-methoxy-benzoylthio)ethylidene]bis[phosphonic acid];
[2-(p-amino-benzoylthio)ethylidene]bis[phosphonic acid];
[2-(acetylthio)ethylidene]bis[phosphonic acid] disodium Salt;
[2-mercapto-2-(phenyl)ethylidene]bis[phosphonic acid];
[2-mercapto-2-(o-aminophenyl)ethylidene]bis[phosphonic acid];
[2-mercapto-2-(m-aminophenyl)ethylidene]bis[phosphonic acid];
[2-mercapto-2-(p-aminophenyl)ethylidene]bis[phosphonic acid];
[2-Acetylthio-2-(phenyl)ethylidene]bis[phosphonic acid];
[3-mercapto-1-hydroxybutylidene]bis[phosphonic acid];
[3-mercapto3-methyl-1-hydroxybutylidene]bis[phosphonic acid];
[4-amino-3-mercapto-1-hydroxybutylidene]bis[phosphonic acid];
[4-amino-2-mercapto-1-hydroxybutylidene]bis[phosphonic acid];
[2-amino-1-hydroxy-3-mercapto-3-methylbutylidene]bis [phosphonic acid];
[2-amino-1-hydroxy-3-acetylthio-3-methylbutylidene]bis [phosphonic acid]; 1-[(Hydroxy)methylphosphinyl]-2-mercaptoethylphosphonic acid;
[2-Mercapto-2-methylpropylidene]bis[phosphonic acid];
[2-(Acetylthio)-2-methylpropylidene]bis[phosphonic acid] Disodium Salt;
[1-Hydroxy-2-(2-acetylthiocyclohexyl)ethylidene]bis [phosphonic acid];
[1-Hydroxy-2-(3-acetylthiocyclohexyl)ethylidene]bis [phosphonic acid];
[1-Hydroxy-2-(4-acetylthiocyclohexyl)ethylidene]bis [phosphonic acid];
[1-Hydroxy-2-(2-mercaptocyclohexyl)ethylidene]bis [phosphonic acid];
[1-Hydroxy-2-(3-mercaptocyclohexyl)ethylidene]bis [phosphonic acid];
[1-Hydroxy-2-(4-mercaptocyclohexyl)ethylidene]bis [phosphonic acid];
[1-Hydroxy-2-(2-(3-mercaptopropyl)cyclohexyl) ethylidene]bis[phosphonic acid];
[1-Hydroxy-2-(3-(2-mercaptoethyl)cyclohexyl)ethylidene] bis[phosphonic acid];
[1-Hydroxy-2-(2-acetylthiocyclopentyl)ethylidene]bis [phosphonic acid];
[1-Hydroxy-2-(3-acetylthiocyclopentyl)ethylidene]bis [phosphonic acid];
[1-Hydroxy-2-(2-mercaptocyclopentyl)ethylidene]bis [phosphonic acid];
[1-Hydroxy-2-(3-mercaptocyclopentyl)ethylidene]bis [phosphonic acid];
[1-Hydroxy-2-(2-(2-mercaptoethyl)cyclopentyl)ethylidene] bis[phosphonic acid]; [1-Hydroxy-2-(2-(3-mercaptopropyl)cyclopentyl)ethylidene]bis[phosphonic acid];
[2-Mercapto-5-phenylpentylidene]bis[phosphonic acid];
[2-Mercapto-5-(o-aminophenyl)pentylidene]bis[phosphonic acid];
[2-Mercapto-5-(m-aminophenyl)pentylidene]bis [phosphonic acid];
[2-Mercapto-5-(p-aminophenyl)pentylidene]bis[phosphonic acid];
[2-Mercapto-5-phenylbutylidene]bis[phosphonic acid];
[2-Mercapto-5-(o-aminophenyl)butylidene]bis[phosphonic acid];
[2-Mercapto-5-(m-aminophenyl)butylidene]bis[phosphonic acid];
[2-Mercapto-5-(p-aminophenyl)butylidene]bis[phosphonic acid];
[2-Acetylthio-5-phenylpentylidene]bis[phosphonic acid];
[2-acetylthio-5-(p-aminophenyl)pentylidene]bis [phosphonic acid];

[3-(3-furfuryl)-2-mercaptoethylidene]bis[phosphonic acid];
[3-cyclohexyl-2-mercaptopropylidene]bis[phosphonic acid];

In order to determine and assess pharmacological activity, testing of the diphosphonate compounds in animals is carried out using various assays known to those skilled in the art. Thus, the In vivo bone antiresorptive activity may be conveniently demonstrated using an assay designed to test the ability of these compounds to inhibit the resorption of bone, which bone resorption is characteristic of abnormal calcium and phosphate metabolism. Examples of such known tests include the Schenk model rat model and the adjuvant arthritis test. Also useful is the in vitro hydroxyapatite crystal growth inhibition test. These and other appropriate tests for pharmacological activity are disclosed and/or referred to in Shinoda et al., *Calcified Tissue International*, 35, pp 87–99 (1983); Schenk et al., *Calcified Tissue Research*, 11, pp 196–214 (1973); Russell et al., *Calcified Tissue Research*, 6, pp 183–196 (1970); Muhlbauer and Fleisch, *Mineral Electrolyte Metab.*, 5, pp 296–303 (1981); Nancollas et al., *Oral Biol.*, 15, 731 (1970); U.S. Pat. No. 3,683,080, to Francis, issued Aug. 8, 1972; U. S. Pat. No. 4,134,969, to Schmidt-Dunker, issued Jan. 16, 1979; and EPO Patent Application Publication No. 189,662, published Aug. 6, 1986; the disclosures of all these articles and patent specifications being incorporated herein by reference in their entirety. Certain of these tests for pharmacological activity are also described in more detail in the Examples provided hereinafter.

In addition to being useful for treating or preventing pathological conditions characterized by abnormal calcium or phosphate metabolism, the compounds of the present invention may have other uses. For example, the compounds of the present invention are believed to be useful as bone scanning agents after labeling with 99m-technetium. In addition, the compounds of the present invention are useful as sequestering agents for polyvalent metal ions, particularly di- (e.g. calcium and magnesium) and trivalent metal ions (e.g. indium). Thus, the compounds of the present invention are useful as builders in detergents and cleansers, or for treating water. They are also useful as stabilizers for compounds. In addition, they may be useful in preventing the formation of tartar (i.e., calculus) and/or plaque on teeth. Finally, the compounds of the present invention may be useful as herbicides which are non-toxic to animals.

The phosphonate compounds of the present invention can be made utilizing the methods set forth in Examples A–R herein.

Pharmaceutical Compositions Containing Phosphonate Compounds

The phosphonate compounds described herein may be administered to humans or other mammals by a variety of routes, including, but not limited to, oral dosage forms and injections (intravenous, intramuscular, intraperitoneal and subcutaneous). Numerous other dosage forms containing the novel thio-substituted phosphonate compounds of the present invention can be readily formulated by one skilled in the art, utilizing the suitable pharmaceutical excipients as defined below. For considerations of patient compliance, oral dosage forms are generally most preferred.

The term "pharmaceutical composition" as used herein means a combination comprised of a safe and effective amount of the thio-substituted phosphonate compound active ingredient, or mixtures thereof, and pharmaceutically-acceptable excipients.

The phrase "safe and effective amount", as used herein, means an amount of a compound or composition large enough to significantly positively modify the symptoms and/or condition to be treated, but small enough to avoid serious side effects (at a reasonable benefit/risk ratio), within the scope of sound medical judgment. The safe and effective amount of active ingredient for use in the pharmaceutical compositions to be used in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically-acceptable excipients" as used herein includes any physiologically inert, pharmacologically inactive material known to one skilled in the art, which is compatible with the physical and chemical characteristics of the particular phosphonate compound active ingredient selected for use. Pharmaceutically-acceptable excipients include, but are not limited to, polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

The term "oral dosage form" as used herein means any pharmaceutical composition intended to be systemically administered to an individual by delivering said composition to the gastrointestinal tract of an individual, via the mouth of said individual. For purposes of the present invention, the delivered form can be in the form of a tablet, coated or non-coated; solution; suspension; or a capsule, coated or non-coated.

The term "injection" as used herein means any pharmaceutical composition intended to be systemically administered to a human or other mammal, via delivery of a solution or emulsion containing the active ingredient, by puncturing the skin of said individual, in order to deliver said solution or emulsion to the circulatory system of the individual either by intravenous, intramuscular, intraperitoneal or subcutaneous injection.

The rate of systemic delivery can be satisfactorily controlled by one skilled in the art, by manipulating any one or more of the following:

(a) the active ingredient proper;
(b) the pharmaceutically-acceptable excipients; so long as the variants do not interfere in the activity of the particular active ingredient selected;
(c) the type of the excipient, and the concomitant desirable thickness and permeability (swelling properties) of said excipients;
(d) the time-dependent conditions of the excipient itself and/or within the excipients;
(e) the particle size of the granulated active ingredient; and
(f) the pH-dependent conditions of the excipients.

In particular, the solubility, acidity, and susceptibility to hydrolysis of the different thio-substituted phosphonate active ingredients, such as acid addition salts, salts formed with the carboxylic group, e.g., alkali metal salts, alkaline earth metal salts, etc., and esters, e.g., alkyl, alkenyl, aryl, aralkyl, may be used as guidelines for the proper choice. In addition, suitable pH-conditions might be established within the oral dosage forms by adding a suitable buffer to the active ingredient in accordance with the desired release pattern.

As stated hereinabove, pharmaceutically-acceptable excipients include, but are not limited to, resins, fillers, binders, lubricants, solvents, glidants, disintegrants co-solvents, surfactants, preservatives, sweetener agents, flavoring agents, buffer systems, pharmaceutical-grade dyes or pigments, and viscosity agents.

The preferred solvent is water.

Flavoring agents among those useful herein include those described in *Remington's Pharmaceutical Sciences*, 18th Edition, Mack Publishing Company, 1990, pp. 1288–1300, incorporated by reference herein. The pharmaceutical compositions suitable for use herein generally contain from 0–2% flavoring agents.

Dyes or pigments among those useful herein include those described in *Handbook of Pharmaceutical Excipients*, pp. 81–90, 1986 by the American Pharmaceutical Association & the Pharmaceutical Society of Great Britain, incorporated by reference herein. The pharmaceutical compositions herein generally contain from 0–2% dyes or pigments.

Preferred co-solvents include, but are not limited to, ethanol, glycerin, propylene glycol, polyethylene glycols. The pharmaceutical compositions of the present invention include from 0–50% co-solvents.

Preferred buffer systems include, but are not limited to, acetic, boric, carbonic, phosphoric, succinic, malaic, tartaric, citric, acetic, benzoic, lactic, glyceric, gluconic, glutaric and glutamic acids and their sodium, potassium and ammonium salts. Particularly preferred are phosphoric, tartaric, citric, and acetic acids and salts. The pharmaceutical composition of the present invention generally contain from 0–5% buffer systems.

Preferred surfactants include, but are not limited to, polyoxyethylene sorbitan fatty acid esters, polyoxyethylene monoalkyl ethers, sucrose monoesters and lanolin esters and ethers, alkyl sulfate salts, sodium, potassium, and ammonium salts of fatty acids. The pharmaceutical compositions of the present invention include 0–2% surfactants.

Preferred preservatives include, but are not limited to, phenol, alkyl esters of parahydroxybenzoic acid, o-phenylphenol benzoic acid and the salts thereof, boric acid and the salts thereof, sorbic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben. The compositions of the present invention generally include from 0–2% preservatives.

Preferred sweeteners include, but are not limited to, sucrose, glucose, saccharin, sorbitol, mannitol, and aspartame. Particularly preferred are sucrose and saccharin. Pharmaceutical compositions of the present invention include 0–5% sweeteners.

Preferred viscosity agents include, but are not limited to, methylcellulose, sodium carboxymethylcellulose, hydroxypropylmethylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions of the present invention include 0–5% viscosity agents.

Preferred fillers include, but are not limited to, lactose, mannitol, sorbitol, tribasic calcium phosphate, dibasic calcium phosphate, compressible sugar, starch, calcium sulfate, dextro and microcrystalline cellulose. The compositions of the present invention contain from 0–75% fillers.

Preferred lubricants include, but are not limited to, magnesium stearate, stearic acid, and talc. The pharmaceutical compositions of the present invention include 0.5–2% lubricants.

Preferred glidants include, but are not limited to, talc and colloidal silicon dioxide. The compositions of the present invention include from 1–5% glidants.

Preferred disintegrants include, but are not limited to, starch, sodium starch glycolate, crospovidone, croscarmelose sodium, and microcrystalline cellulose. The pharmaceutical compositions of the present invention include from 4–15% disintegrants.

Preferred binders include, but are not limited to, acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. The compositions of the present invention include 1–10% binders.

Compounds of the present invention may comprise from about 0.1% to about 99.9% by weight of the pharmaceutical compositions of the present invention. Preferably, the compounds of the present invention comprise from about 15% to about 95% by weight of the pharmaceutical compositions of the present invention.

Accordingly, the pharmaceutical compositions of the present invention include from 15–95% of a thio-substituted phosphonate compound active ingredient, or mixture, thereof; 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

The choice of a pharmaceutical excipient to be used in conjunction with the thio-substituted phosphonates of the present compositions is basically determined by the way the phosphonate compound is to be administered. If the compound is to be injected, the preferred pharmaceutical carrier is sterile, physiological saline, the pH of which has been adjusted to about 7.4. However, the preferred mode of administering the phosphonates of the present invention is orally, and the preferred unit dosage form is therefore tablets, capsules and the like, comprising from about 0.1 mg P to about 600 mg P of the diphosphonic acid compounds described herein. Pharmaceutical carriers suitable for the preparation of unit dosage forms for oral administration are well known in the art. Their selection will depend on secondary considerations like taste, cost, and shelf stability, which are not critical for the purposes of the present invention, and can be made without difficulty by a person skilled in the art.

The term "mg P", as used herein, means the weight of the phosphorus atoms present in an amount of a diphosphonic acid compound of the present invention. This unit is used to standardize the amount of the diphosphonic acid compounds of the present invention to be used in the pharmaceutical compositions and methods of the present inventions. For example, 2-(acetylthio)ethylidene bis[phosphonic acid] disodium salt has a molecular weight of 308 g/mole, of which 20% (62 g/mole) is due to the two phosphorus atoms present in this molecule. One milligram of this compound is therefore calculated to have 0.20 mg P (1 mg×20.0%). Thus, to prepare a pharmaceutical composition containing 1 mg P of this compound, the composition should contain 5 mg of the compound; and to dose 1 mg P/kg of this compound to a 50 kg patient, the patient would be dosed with 250 mg of this compound.

The pharmaceutically-acceptable carrier employed in conjunction with the phosphonates of the present invention is used at a concentration sufficient to provide a practical size to dosage relationship. Preferably, the pharmaceutically-acceptable carriers, in total, may comprise from about 0.1% to about 99.9% by weight of the total composition, more preferably from about 15% to about 95%, and most preferably from about 20% to about 80%.

Suitable pharmaceutical compositions are described herein in Examples U–W. It is well within the capabilities of one skilled in the art to vary the non-limiting examples described herein to achieve a broad range of pharmaceutical compositions.

Method for Treating or Preventing Diseases Characterized by Abnormal Calcium and Phosphate Metabolism Another aspect of the present invention is methods for treating or preventing diseases characterized by abnormal calcium and phosphate metabolism. Such methods comprise administering to a human or lower animal in need of such treatment a safe and effective amount of diphosphonate compound described herein.

The preferred mode of administration is oral, but other known methods of administration are contemplated as wall, e.g., dermatomucosally (for example, dermally, rectally and the like) and parenterally (for example, by subcutaneous injection, intramuscular injection, intra-articular injection, intravenous injection and the like). Inhalation is also included. Thus, specific modes of administration include, without limitation, oral, transdermal, mucosal, sublingual, intramuscular, intravenous, intraperitoneal, and subcutaneous administration, as well as topical application.

The term "abnormal calcium and phosphate metabolism", as used herein, means (1) conditions which are characterized by anomalous mobilization of calcium and phosphate leading to general or specific bone loss, or excessively high calcium and phosphate levels in the fluids of the body; and (2) conditions which cause or result from deposition of calcium and phosphate anomalously in the body. The first category includes, but is not limited to, osteoporosis, Paget's disease, hyperparathyroidism, hypercalcemia of malignancy, heterotopic ossification, and osteolytic bone metastases. The second category includes, but is not limited to, myositis ossificans progressive, calcinosis universalis, and such afflictions as arthritis, rheumatoid arthritis, osteoarthritis, neuritis, bursitis, tendonitis and other which predispose involved tissue to deposition of calcium and phosphate.

The term "rheumatoid arthritis" as used herein, means a chronic systemic and articular inflammatory disorder of unknown etiology. It is characterized by destruction of articular cartilage, ligaments, tendons, and bone.

The term "osteoarthritis" as used herein, means a non-inflammatory disorder of the movable joints. It is characterized by deterioration and abrasion of the articular cartilage; and new bone formation at the joint surface.

The terms "person at risk" and "person in need of such treatment", as used herein, mean any human or other mammal which suffers a significant risk of abnormal calcium and phosphate metabolism if left untreated, and any human or other mammal diagnosed as being afflicted with abnormal calcium and phosphate metabolism. For example, postmenopausal women; persons undergoing certain steroid therapy; persons on certain anti-convulsant drugs; persons diagnosed as having Paget's disease, hyperparathyroidism, hypercalcemia of malignancy, or osteolytic bone metastases; persons diagnosed as suffering from one or more of the various forms of osteoporosis; persons belonging to a population group known to have a significantly higher than average chance of developing osteoporosis, e.g., postmenopausal women, men over age 65, and persons being treated with drugs known to cause osteoporosis as a side effect; persons diagnosed as suffering from myositis ossificans progressiva or calcinosis universalis; and persons afflicted with arthritis, osteoarthritis, neuritis, bursitis, tendonitis and other inflammatory conditions which predispose involved tissue to deposition of calcium and phosphate.

The phrase "safe and effective amount", as used herein, means an amount of a compound or composition of the present invention high enough to significantly positively modify the condition to be treated, but low enough to avoid serious side effects (at a reasonable benefit/risk ratio), within the scope of sound medical judgment. The safe and effective amount of diphosphonate compounds of the present invention will vary with the particular condition being treated, the age and physical condition of the patient being treated, the severity of the condition, the duration of the treatment, the nature of concurrent therapy, the specific phosphonate employed, the particular pharmaceutically-acceptable excipients utilized, and like factors within the knowledge and expertise of the attending physician. However, single dosages can range from about 0.01 mg P to about 3500 mg P, or from about 0.0002 to about 70 mg P/kg of body weight (based on a body weight of 50 kg). Preferred single dosages are from about 1 mg P to about 600 mg P, or from about 0.02 to about 12 g P/kg of body weight (based on a body weight of 50 kg). Up to about four single dosages per day may be administered. Daily dosages greater than about 500 mg P/kg are not required to produce the desired effect and may produce undesirable side effects. The higher dosages within this range are, of course, required in the case of oral administration because of limited absorption.

The following Examples further describe and demonstrate the preferred embodiments within the scope of the present invention. The Examples are given solely for the purpose of illustration, and are not to be construed as limitations of the present invention since many variations thereof are possible without departing from its spirit and scope.

EXAMPLE A

Synthesis of [2-[(2,2-dimethyl-1-oxopropyl)thio]ethylidene]bis[Phosphonic Acid]

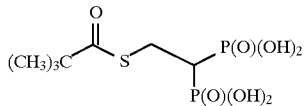

I. Synthesis [2-[(2,2-dimethyl-1-oxopropyl)thio]-ethylidene]bis[phosphonic acid] tetraethyl ester Tetraethyl ethenylidenebis(phosphonate) (3.00 g, 10.0 mmol) [prepared as described by C. R. Degenhardt and D. C. Burdsall, *J. Org. Chem.*, Vol. 51, pp. 3488–3490 (No.18) 1986] and pivalic acid (1.54 9, 13.0 mmol) are stirred in chloroform (50 ml) at room temperature for 96 hours. The reaction mixture is evaporated under reduced pressure to give the thioester (4.04 g) as a pale yellow oil in 98% yield.

II. Synthesis of [2-[(2,2-dimethyl-1-oxopropyl)thio]ethylidene]-bis[phosphonic acid]

The thioester (4.00 g, 9.84 mmol) is stirred with bromotrimethylsilane (15.06 g, 98.4 mmol) in chloroform (40 ml)

at room temperature for 120 hours. The reaction mixture is quenched by the addition of methanol (40 ml) then concentrated under reduced pressure. The residue is triturated in hexanes and the product is collected by filtration and dried in a vacuum desiccator to provide the bisphosphonic acid (2.21 g) in 69% yield.

EXAMPLE B

Synthesis of [2-(Benzoylthio)ethylidene]bis [Phosphonic Acid]

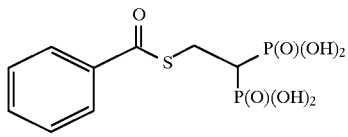

I. Synthesis of [2-(Benzoylthio)ethylidene]bis[phosphonic acid] tetraethyl ester To Tetraethyl ethenylidenebis(phosphonate) (5.25 g, 17.43 mmol) [prepared as described by C. R. Degenhardt and D. C. Burdsall, *J. Org. Chem.*, Vol. 51, pp. 3488–3490 (No.18) 1986] in chloroform (50 ml) is added thiobenzoic acid (2.65 g, 19.17 mmol). The reaction mixture is stirred at room temperature under an atmosphere of nitrogen for 4 days. The reaction is then washed with water (2×100 ml) followed by saturated aqueous NaCl (1×100 ml). The organic layer is dried over sodium sulfate, filtered and concentrated under reduced pressure to provide the thioester in an 87% yield as a yellow oil (6.6 g).

II. Synthesis of [2-(Benzoylthio)ethylidene]bis[phosphonic acid]

The phosphonate esters are hydrolyzed under anhydrous conditions by treatment of the tetra ethyl bisphosphonate (4.15 g, 9.47 mmol) with 10 equivalents of bromotrimethylsilane (14.5 g, 94.7 mmol) in chloroform (150 ml) at room temperature for 48 hours. The reaction mixture is then stirred for 30 minutes with water (20 ml) and ethyl acetate (20 ml). The layers are separated and the aqueous layer is treated with charcoal, filtered and concentrated to provide the bisphosphonic acid in 43% yield (1.3 g).

EXAMPLE C

Synthesis of [2-(Acetylthio)ethylidene]bis [Phosphonic Acid] Disodium Salt

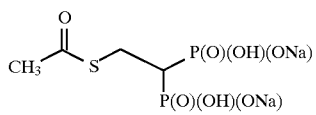

Tetrasodium ethenylidenebis(phosphonate) (2.76 g, 10 mmol) [prepared as described in R. L. Carroll, U.S. Pat. No. 3,686,290 (1972) and in R. L. Carroll and M. M. Crutchfield, Canadian Patent 811,736 (1969)] and thiolacetic acid (3.81 g, 50 mmol) are dissolved in water (20 ml) and stirred at room temperature under an atmosphere of nitrogen for 20 hours. The reaction mixture is then concentrated under reduced pressure and further dried under vacuum overnight. The solid product is triturated in warm ethanol, cooled and filtered while washing with diethyl ether to yield pure product as a pale yellow solid.

EXAMPLE D

Synthesis of [2-mercapto-2-(phenyl)ethylidene]bis [Phosphonic Acid]

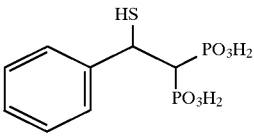

I. Synthesis of 4,4'-(phenylmethylene)bismorpholine

A suspension of benzene (10 ml) containing 3-pyridine carboxaldehyde (3.97 g, 37.09 mmol), boron trioxide (4.31 9, 61.94 mmol) and morpholine (7.76 g, 89.02 mmol) is stirred at room temperature for 2 hours. The reaction mixture is filtered through celite to remove the hydrated boron complex and the filtrate is concentrated under reduced pressure to provide a 73% yield of the bisaminal (7.17 9) in good purity.

II. Synthesis of [2-phenylethenylidene]bis[phosphonic acid] tetraethyl ester

To the bisaminal (5.0 g, 19.1 mmol) in toluene (30 ml) is added trifluoroacetic acid (4.45 9, 39 mmol). The mixture is heated for 15 minutes at 60° C., tetraethyl methylene diphosphonate (5.49 g, 19.0 mmol) is added and the reaction is stirred for a total of 22 hours at 60° C. The reaction mixture is cooled and water is added. The layers are separated and the aqueous layer is extracted with methylene chloride (3×15 ml). The organic layers are combined, dried over sodium sulfate, filtered and concentrated under reduced pressure. The bisphosphonate is separated from unreacted methylene diphosphonate and pyridine carboxaldehyde by flash chromatography on silica gel (97:3 methylene chloride/isopropylalcohol) to provide the vinyl adduct (3.84 g) in 49% yield as a pale yellow oil.

III. Synthesis of [2-acetylthio-2-(phenyl)ethylidene]bis [phosphonic acid] tetraethyl ester

[2-phenylethenylidene]bis[phosphonic acid] tetraethyl ester (3.83 g, 10.19 mmol) and thiolacetic acid (0.85 g, 11.21 mmol) are stirred in anhydrous chloroform (100 ml) for 48 hours at room temperature. The reaction mixture is then concentrated under reduced pressure. The residue was dissolved in acetone and concentrated a second time under vacuum to provide [2-acetylthio-2-(phenyl)ethylidene] (1.01 g) in good purity.

IV. Synthesis of [2-mercapto-2-(phenyl)ethylidene]bis [phosphonic acid]

A solution of the thioacetate (0.50 9, 1.11 mmol) in concentrated hydrochloric acid (6 ml) is heated at reflux overnight. The reaction is evaporated to dryness under vacuum. Acetone is added to the residue and the mixture is evaporated to dryness a second time to provide the desired product (0.10 g) in 30% yield.

EXAMPLE E

Synthesis of [2-Acetylthio-2-(phenyl)ethylidene]bis [Phosphonic Acid]

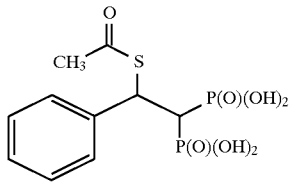

I. Synthesis of [3-(2-Phenyl)ethenylidene]bis[phosphonic acid]

[2—Phenylethenylidene]bis[phosphonic acid] tetraethyl ester [prepared as described in Example D (part II) hereinbefore] (5.25 mmol) is treated with bromotrimethylsilane (42.00 mmol) in chloroform (175 ml) at 50° C. for 12 hours under an atmosphere of nitrogen. The reaction mixture is then stirred for 30 minutes with water (50 ml) and ethyl acetate (50 ml). The layers are separated and the aqueous layer is treated with charcoal, filtered through celite and concentrated to provide the bisphosphonic acid as a pale yellow solid.

IV. Synthesis of [2-Acetylthio-2-(3-phenyl) ethylidene]bis[phosphonic acid]

To [3-(2-phenyl)ethenylidene]bis[phosphonic acid] (2.50 mmol) in water (10 ml) is added thioacetic acid (12.50 mmol). After stirring at room temperature for 5 hours, the reaction mixture is concentrated under reduced pressure, triturated with acetone and then dried under high vacuum to provide the bisphosphonic acid as a pale yellow solid.

EXAMPLE F

Synthesis of [3-Mercapto-1-hydroxybutylidene]bis [Phosphonic Acid]

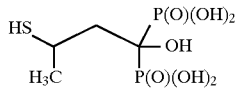

I. Synthesis of 3-Acetylthiocrotonic Acid

A solution of crotonic acid (4.30 g, 50 mmol) and thiolacetic acid (5.71 g, 57.5 mmol) in anhydrous hexanes (12.5 ml) is heated at reflux for 24 hours. The reaction mixture is then concentrated under reduced pressure to provide the thioacetate (8.11 g) which can be used without further purification.

II. Synthesis of 3-Acetylthiocrotonyl Chloride

To a solution of 3—acetylthiocrotonic acid (8.0 g, 49.3 mmol) in methylene chloride (50 ml) is added a solution of oxalyl chloride (39.5 g, 247 mmol) in methylene chloride (25 ml). The reaction mixture is stirred at room temperature under an atmosphere of nitrogen for 18 hours. The solvents are removed by distillation, more methylene chloride is added and the reaction is further dried by rotary evaporation under reduced pressure to provide the acid chloride (5.28 g).

III. Synthesis of 3-Acetylthio-1-oxobutylphosphonic acid dimethyl ester

To the acid chloride (4.28 g, 23.7 mmol) at 0° C. is added slowly trimethyl phosphite (2.94 g, 23.7 mmol). The reaction is allowed to warm to room temperature and stirred overnight. The reaction mixture is vacuum dried to provide the desired product (4.0 g) is suitable purity.

IV. Synthesis of [3-Acetylthio-1-hydroxybutylidene]bis [phosphonic acid] tetramethyl ester To the phosphonate (3.0 g, 18.0 mmol) at 0° C. is added dimethyl phosphite (2.28 g, 20.6 mmol). The reaction mixture is then heated to 55°–65° C. and stirred for 48 hours. The desired product is purified by flash chromatography with 10% isopropanol in methylene chloride on silica gel.

V. Synthesis of [3-Mercapto-1-hydroxybutylidene]bis [phosphonic acid]

[3-Acetylthio-1-hydroxybutylidene]bis[Phosphonic Acid]tetramethyl ester (4.0 g, 1.1 mmol) is heated at reflux in concentrated hydrochloric acid (8 ml) for 7 hours under an atmosphere of nitrogen. The reaction mixture is concentrated under reduced pressure and the desired product (0.28 g) is obtained in a 94% yield upon further drying in a vacuum desiccator.

EXAMPLE G

1-[(Hydroxy)methylphosphinyl]-2-mercaptoethylphosphonic Acid

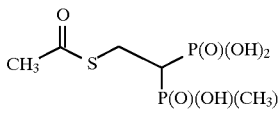

I. Synthesis of (Ethenylidene)phosphonomethylphosphonic acid, triethyl ester

Using essentially the same procedure as described in C. R. Degenhardt and D. C. Burdsall, *J. Org. Chem.*, Vol. 51, pp. 3400–3490 (No. 18) 1986, methylenephosphonomethylphosphinic acid, triethyl ester [prepared as described in H. G. Henning and G. Petzold, *Z. Chem.*, vol. 5, pp. 419 (1965)] is converted to (ethenylidene)phosphonomethylphosphinic, triethyl ester.

II. Synthesis of 1-[(Hydroxy)methylphosphinyl]-2-(acetylthio) ethylphosphonic acid, triethyl ester A solution of (ethenylidene)phosphonomethylphosphinic acid, triethyl ester (11.62 g, 43.0 mmol) and thiolacetic acid (3.27 g, 43.0 mmol) in anhydrous chloroform (116 ml) is stirred at room temperature for 72 hours. The reaction mixture is evaporated under reduced pressure to provide the desired product (8.3 g) as a pale yellow oil.

III. Synthesis of 1-[(Hydroxy)methylphosphinyl]-2-mercaptoethyl phosphonic acid

1-[(Hydroxy)methylphosphinyl]-2-(acetylthio) phosphonic acid, triethyl ester (8.3 g) is heated at reflux in concentrated hydrochloric acid (130 ml) for 7 hours under an atmosphere of nitrogen. The reaction mixture is concentrated under reduced pressure to provide 1-[(hydroxy) methylphosphinyl]-2-mercaptoethylphosphonic acid.

EXAMPLE H

Synthesis of [2-Mercapto-2-methylpropylidene]bis [Phosphonic Acid]

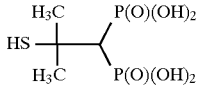

I. Synthesis of 2—Methylpropylphosphonic acid, dimethyl ester

A solution of 1-bromo-2-methylpropane (100.0 g, 0.73 mol) and trimethyl phosphite (135.7 g, 1.09 mmol) is heated at 90° C. for 72 hours while maintaining a flow of nitrogen through the reaction. The excess trimethyl phosphite is removed by distillation and the crude residue is chromatographed with 2% isopropanol in methylene chloride on silica gel. The product can be used in the following reaction without further purification.

II. Synthesis of [2-Methylpropylidene]bis[phosphonic acid] diethyl dimethyl ester To a solution of 2—methylpropylphosphonic acid, dimethyl ester (2.20 g, 14.47 mmol) in anhydrous THF (200 ml) is added sec-butyllithium (20.04 ml, 26.05 mmol, 1.3M in cyclohexane) at 0° C. Following the addition, stirring is continued for an additional 30 minutes. This solution is then slowly added to a solution of diethyl chlorophosphate (2.50 9, 14.47 mmol) in anhydrous THF (100 ml) at room temperature. After stirring the reaction overnight, the mixture is quenched by the addition of a saturated aqueous solution of sodium bicarbonate and then extracted with methylene chloride. The combined organic extracts are dried over anhydrous sodium sulfate, filtered and concentrated under reduced pressure. The crude product is purified by flash chromatography with 30% acetone in hexanes on silica gel.

III. Synthesis of [2-Methyl-1-phenylthiopropylidenel bisphosphonic acid] diethyl dimethyl ester To a mixture of 35% KH in mineral oil (0.42 g, 3.68 mmol) in anhydrous toluene (75 ml) at 0° C. is added dropwise a solution of [2-methylpropylidene]bis [phosphonic acid] diethyl dimethyl ester (1.05 g, 3.48 mmol) in toluene (25 ml). The reaction is allowed to warm to room temperature and stirred an additional 60 minutes. To this is added dropwise a solution of phenyl disulfide (0.80 g, 3.68 mmol) is toluene (25 ml). After stirring overnight at room temperature, the reaction mixture is diluted with water and extracted with diethyl ether. The combined organic extracts are dried over sodium sulfate, filtered and concentrated under reduced pressure. The crude product is purified by flash chromatography with 5% isopropanol in methylene chloride on silica gel.

IV. Synthesis of [2-Methyl-1-propenyldiene]bis[phosphonic acid] diethyl dimethyl ester To a solution of [2-methyl-1-(phenylthio)propylidene]bis [phosphonic acid] diethyl dimethyl ester (2.31 g, 5.63 mmol) in anhydrous chloroform (65 ml) at 0° C. is added dropwise a solution of 3—chloroperoxybenzoic acid (1.07 g, 6.19 mmol) in chloroform (25 ml). After stirring at 0° C. for 2 hours, a solution of 10% aqueous sodium sulfite is added and the mixture is stirred vigorously for an additional 10 minutes. The layers are then separated and the aqueous layer is extracted with more chloroform. The organic extracts are combined and then washed with a saturated aqueous solution of sodium bicarbonate, followed by a saturated aqueous solution of sodium chloride. The organic extracts are dried over sodium sulfate, filtered and concentrated under reduced pressure. The crude residue is purified by flash chromatography with 50% acetone in hexanes on silica gel.

V. Synthesis of [2-Acetylthio-2-methyl-1-propylidene]bis [phosphonic acid] diethyl dimethyl ester To a solution of [2-methyl-1-propenyldiene]bis [phosphonic acid] diethyl dimethyl ester (0.55 g, 1.83 mmol) in anhydrous chloroform (50 ml) is added thiolacetic acid (0.17 g, 2.28 mmol). The reaction mixture is stirred at room temperature under an atmosphere of nitrogen for 72 hours then concentrated under reduced pressure. Acetone is added to the crude residue and the mixture is evaporated to dryness a second time. The product can be used in the next step without further purification.

VI. Synthesis of [2-Mercapto-2-methylpropylidene]bis [phosphonic acid] Disodium Salt The thioacetate (0.50 g, 1.33 mmol) is heated at reflux in concentrated hydrochloric acid (10 ml) under an atmosphere of nitrogen for 3 hours. The reaction mixture is then concentrated under reduced pressure. The desired product is obtained by recrystallizing the crude solid residue in water and ethanol.

EXAMPLE I

Synthesis of [2-(Acetylthio)-2-methyloropylidene] bis[Phosphonic Acid] Disodium Salt

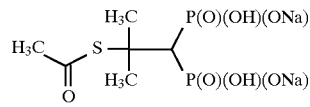

I. Synthesis of [2-Methyl-1-propenyldiene]bis[phosphonic acid] Tetrasodium salt

To a solution of [2-methyl-1-propenyldiene]bis [phosphonic acid] diethyl dimethyl ester [prepared as described in Example H (part IV) hereinbefore] (1.25 g, 4.17 mmol) in anhydrous chloroform (50 ml) is added freshly distilled bromotrimethyl-silane (6.38 g, 41.7 mmol). The reaction mixture is heated at 50° C. for 5 hours. Ethyl acetate (10 ml) and water (25 ml) is added and the reaction mixture is stirred vigorously for 30 minutes. The layers are separated and the aqueous layer is treated with charcoal, filtered and concentrated under reduced pressure. The crude residue is triturated with diethyl ether then further dried overnight under vacuum. The solid residue is dissolved in water and brought to pH 12 by the addition of IN NaOH. The product is precipitated by the addition of ethanol and collected by filtration.

II. Synthesis of [Z-(Acetylthio)-2-methylpropylidene]-bis [phosphonic acid] Disodium Salt

[2-Methyl-1-propenyldiene]bis[phosphonic acid] tetrasodium salt (1.10 g, 4.23 mmol) and thiolacetic acid (1.61 g, 21.15 mmol) are dissolved in water (15 ml) and stirred at room temperature under an atmosphere of nitrogen for 20 hours. The reaction mixture is then concentrated under reduced pressure and further dried under vacuum overnight. The solid product is triturated in warm ethanol, cooled and filtered while washing with diethyl ether to yield pure product as a pale yellow solid.

EXAMPLE J

Synthesis of [1-Hydroxy-2-(2-acetylthiocyclohexyl) ethylidene]bis[Phosphonic Acid]

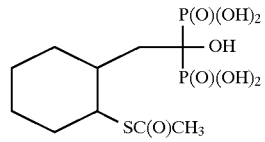

I. Synthesis of [2-(1-Cyclohex-1-enyl)-1-hydroxy]bis [phosphonic acid]

A solution containing 1—cyclohexenyl acetic acid (1.0 mmol), phosphorous acid (2.9 mmol)$_1$ phosphorous trichloride (2.0 mmol) and diethylphosphite (12 mmol) is stirred 30 minutes at room temperature then heated at 60° C. for 24 hours. The reaction mixture is then cooled to room temperature and concentrated hydrochloric acid (50 ml) is added. The reaction mixture is heated at reflux overnight, then cooled to room temperature and filtered through celite and concentrated to dryness under vacuum. The crude product is triturated in ethanol, collected by filtration and air-dried.

II. Synthesis of [1-Hydroxy-2-(2-acetylthiocyclohexyl)ethylidene]-bis[phosphonic acid]

To the bisphosphonic acid (0.75 g, 2.62 mmol) in distilled water (50 ml) is added thiolacetic acid (0.50 g, 6.55 mmol) and the reaction mixture is photolyzed with a sunlamp at room temperature for 72 hours under an atmosphere of nitrogen. After stirring is complete, the reaction mixture is concentrated under reduced pressure and the solid residue is triturated in ethanol. The desired product is obtained in suitable purity following further drying overnight under vacuum.

EXAMPLE K

Synthesis of [1-Hydroxy-2-(2-mercaptocyclohexyl)ethylidene]bis[Phosphonic Acid]

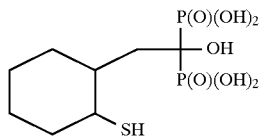

[1-Hydroxy-2-(2-(acetylthio)cyclohexyl)ethylidene]bis[phosphonic acid] is heated at reflux in concentrated hydrochloric acid for 7 hours. The reaction is concentrated under reduced pressure and the solid residue is triturated in ethanol. The product is obtained by recrystallization the crude solid in ethanol and water.

EXAMPLE L

Synthesis of [1-Hydroxy-2-(2-(acetylthio)cyclogentyl)ethylidene]bis[Phosphonic Acid]

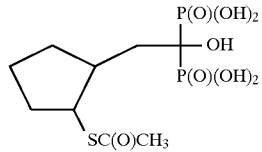

I. Synthesis of [2-(Cyclopent-1-enyl)-1-hydroxy]bis[phosphonic acid]

Using essentially the same procedure as described in Example J (part I), 1-cyclopent-1-enyl acetic acid is converted to [2-(cyclopent-1—enyl)-1-hydroxy]bis[phosphonic acid].

II. Synthesis of [1-Hydroxy-2-(2-acetylthiocyclohexyl)ethylidene]-bis[phosphonic acid]

Using essentially the same procedure as described in Example J (part II), [2-(1-cyclopentenyl)-1-hydroxy]bis[phosphonic acid] is converted to [1-hydroxy-2-(2-acetylthiocyclohexyl)ethylidene] bis[phosphonic acid].

EXAMPLE M

Synthesis of [1-Hydroxy-2-(2-mercaptocyclopentyl)ethylidene]bis[Phosphonic Acid]

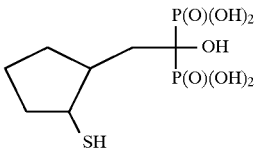

Using essentially the same procedure as described in Example K, [1-hydroxy-2-(2-(acetylthio)cyclohexyl)-ethylidene]bis[phosphonic acid], prepared as described in Example L hereinbefore, is converted to [1-hydroxy-2-(2-mercaptocyclohexyl)-ethylidene]bis[phosphonic acid].

EXAMPLE N

Synthesis of [2-Mercapto-5-phenylpentylidene]bis[Phosphonic Acid]

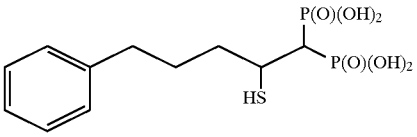

I. Synthesis of [5-phenylpent-1-enylidene]bis[phosphonic acid] diethyl dimethyl ester Using essentially the same procedures as described in Example H (parts I–IV), 5-phenyl-1-chloropentane is converted to [5-phenylpent-1-enylidene]bis[phosphonic acid] diethyl dimethyl ester.

II. Synthesis of [2-acetylthio-5-phenylpentylidene]bis[phosphonic acid] diethyl dimethyl ester To the pentenylidene tetra ester (2.00 mmol) in anhydrous chloroform (75 ml) is added thioacetic acid (2.15 mmol). The reaction is stirred for 22 hours at room temperature under an atmosphere of nitrogen. The reaction mixture is then washed with water followed by a solution of aqueous saturated NaCl. The organic layer is dried over sodium sulfate, filtered and concentrated under reduced pressure. The crude residue can be used without further purification.

III. Synthesis of [2-mercapto-5-phenylpentylidene]bis[phosphonic acid]

The thioacetate (1.5 mmol) is heated at reflux in concentrated hydrochloric acid (15 ml) under an atmosphere of nitrogen for 5 hours. The reaction mixture is then cooled to room temperature, treated with charcoal then filtered through celite. The aqueous filtrate is concentrated under reduced pressure and the crude residue is triturated in acetone. The resulting solid is recrystallized from water and isopropanol to provide [2-mercapto-5-phenylpentylidene]bis[phosphonic acid].

EXAMPLE O

Synthesis of [2-Acetylthio-5-phenylpentylidene]bis[Phosphonic Acid]

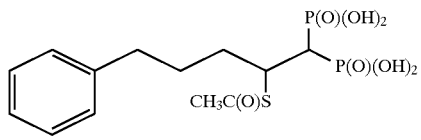

Using essentially the same procedure as described in Example A (part II) hereinbefore, [2-acetylthio-5-phenylpentylidene]bis[phosphonic acid] diethyl dimethyl ester [prepared as described in Example N (part II) hereinbefore] is converted to [2-acetylthio-5-phenylpentylidene]bis[phosphonic acid].

EXAMPLE P

Synthesis of [2-Mercapto-5-(3-aminophenyl)pentylidene]bis[Phosphonic Acid]

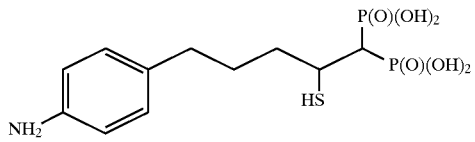

I. Synthesis of [2-mercapto-5-3-nitrophenyl)pentylidene]bis[phosphonic acid] dimethyl diethyl ester Using essentially the same procedure as described in Example H (part I–IV) hereinbefore, 5-(3-nitrophenyl)-1-chloropropane is converted to [5-(3-nitrophenyl)pent-1-enylidene]bis[phosphonic acid] dimethyl diethyl ester.

II. Synthesis of [2-mercapto-5-(3-nitrophenyl)pentylidene]bis[phosphonic acid]

Using essentially the same procedures as described in Example N (part II–III) hereinbefore, [5-(3-nitrophenyl)pent-1-enylidene]bis[phosphonic acid] dimethyl diethyl ester is converted to [2-mercapto-5-(3-nitrophenyl)pentylidene]bis-[phosphonic acid].

II. Synthesis of [2-mercapto-5-(3-aminophenyl)pentylidene]-bis[phosphonic acid]

[2-Mercapto-5-(3-nitrophenyl)pentylidene]bis[phosphonic acid] (0.25 mmol), distilled water (75 ml) and PtO2 (0.20 mg) are placed in a 500 ml Parr hydrogenation bottle. The mixture is hydrogenated at room temperature (40 psi) for 6 hours. The solution is filtered through celite and concentrated under reduced pressure. The resultant solid is triturated in acetone and then further dried overnight in a vacuum desiccator.

EXAMPLE Q

Synthesis of [3-(3-furfuryl)-2-mercaptoethylidene]bis[Phosphonic Acid]

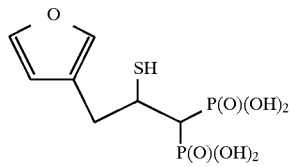

I. Synthesis of 3-(3-furfuryl)prop-1-enylidene]bis[phosphonic acid] diethyl dimethyl ester Using essentially the same procedure as described in Example H (parts I–IV) hereinbefore, 3-(3-furfuryl)-1-chloropropane is converted to 3-(3—furfuryl)prop-1-enylidene]bis[phosphonic acid] diethyl dimethyl ester.

II. Synthesis of [3-(3-furfuryl)-2-mercaptoethylidene]bis[phosphonic acid]

Using essentially the same procedure as described in Example N (part II–III) hereinbefore, 3-(3-furfuryl)prop-1-enylidene]bis[phosphonic acid] diethyl dimethyl ester is converted to [3-(3-furfuryl)-2-mercaptoethylidene]bis[phosphonic acid].

EXAMPLE R

Synthesis of [3-cyclohexyl-2-mercaptopropylidene]bis[Phosphonic Acid]

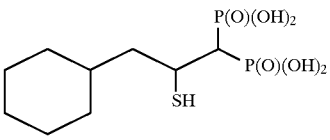

I. Synthesis of [3—(cyclohexyl)prop-1-enylidene]bis[phosphonic acid] dimethyl diethyl ester Using essentially the same procedure as described in Example H (parts I–IV), 3-cyclohexyl-1-chloropropane is converted to [3-(cyclohexyl)prop-1-enylidene]bis[phosphonic acid] diethyl dimethyl ester.

II. Synthesis of [3-cyclohexyl-2-mercaptopropylidene]bis[phosphonic acid]

Using essentially the same procedure as described in Example N (part II–III) hereinbefore, [3-(cyclohexyl)prop-1-enylidene]bis[phosphonic acid] dimethyl diethyl ester is converted to [3-cyclohexyl-2-mercaptopropylidene]bis[phosphonic acid].

EXAMPLE S

Schenk Model

The compounds are evaluated for in vivo bone resorption inhibition and mineralization inhibition in an animal model system known in the field of bone metabolism as the Schenk Model. The general principles of this model system are disclosed in Shinoda et al., *Calcif. Tissue Int.,* 35, 87–99 (1983); and in Schenk et al., *Calcif. Tissue Res.* 11, 196–214 (1973), the disclosures of which are incorporated herein by reference.

Materials and Methods

Animals

Preweaning 17-day-old (30 gms) male Sprague Dawley rats (Charles River Breeding Laboratories) are shipped with their mothers and placed in plastic cages with their mothers upon arrival. At 19 days of age, pups receiving Rat Chow and water a libitum are randomly allocated into treatment or control groups comprising seven animals per group. On day 1 and again on day 7 all animals are given an intraperitoneal ("IP") injection of Calcein (1% solution in 0.9% saline solution; dosed at 0.2 ml/100 g body weight). On day 4 all animals are given an IP injection of tetracycline hydrochloride (1% solution in 0.9% saline solution; dosed at 0.2 ml/100 g body weight). These compounds label actively mineralizing bone and cartilage.

Dose Solutions and Dosing Procedure

All solutions are prepared for subcutaneous injection in 0.9% normal saline and adjusted to pH 7.4 using NaOH and/or HCl. Dose solution calculation is made by considering the mass of powder (based on molecular weight, hydration) of the active material in mg/kg (body weight) that corresponds to mgP/kg. Concentrations are based on dosing 0.2 ml/100 g body weight. Typically, all compounds are administered at 0.01, 0.1, 1.0 and 10.0 mg P/kg/day for 7 days. Compounds showing activity at 0.1 mg P/kg/day are then tested at logarithmic decrements down to 0.001 mg P/kg/day. Adjustments in dosage based on changes in body weight are made on a daily basis.

Necropsy, Tissue Processing and Histomorphometry

On day 8 after the start of dosing, all animals are sacrificed by IP overdose of pentabarbitol. Tibias are dissected free and placed in 70% ethyl alcohol. One tibia is dehydrated in graded ethanol solutions and embedded in methyl methacrylate as described in Schenk, *Methods of Calcified Tissue Preparation* (G. R. Dickson, Editor; Elsevier Science Publ., The Netherlands; 1984), the disclosures of which are incorporated herein by reference in their entirety. The tibia is sectioned longitudinally through the metaphyseal area. Specimens are stained on one surface with silver nitrate and mounted on microscope slides for evaluation with a Quantimet Image Analyzer (Cambridge Instruments, Inc.) using both incandescent and ultraviolet illumination. Metaphyseal trabecular bone content is measured in the region between the fluorescent label and the growth plate: expressed as percent of total area (bone+marrow). Epiphyseal growth plate width is obtained as the mean value of 10 equally-spaced measurements across the section.

Statistical evaluation of data is made using parametric and non-parametric analysis of variance and Wilcoxons rank sum test to determine a statistically significant effect compared to control animals. The Schenk model provides data for in vivo bone resorption inhibition by the compounds.

EXAMPLE T

Adjuvant Arthritis Model

There are numerous animal models of arthritis, among these is adjuvant-induced arthritis using *Mycobacterium butyricum*. This model in a number of ways mimics rheumatoid arthritis in the human (joint swelling associated with cellular and pannus invasion of the joint space, bone resorption, and release of chemotaxic factors and lysosomal constituents into the joint space) (1,2). A number of prophylactic and therapeutic studies have indicated the potential use of anti-inflammatory drugs (3,4) and diphosphonates in arthritis (5,6).

REFERENCES

1. Pearson, C., Wood F. (1959), Studies of Polyarthritis and Other Lesions Induced by Injection of Mycobacterial Adjuvant. 1. General Clinical and Pathological Characteristics and Some Modifying Factors, *Arth. Rheum.*, 2:440–459.
2. Blackman, A., Burns, J. W., Framer, J. B., Radziwonik, H., Westwick, J. (1977), An X-ray Analysis of Adjuvant Arthritis in the Rat. The Effect of Prednisolone and Indomethacin, *Agents and Actions*, 7:145–151.
3. Winter, C. A., Nuss, G. W. (1966), Treatment of Adjuvant Arthritis in Rats with Anti-inflammatory Drugs, *Arth. Rheum.*, 9:394–404.
4. Winder, C. V., Lembke, L. A., Stephens, M. D. (1969), Comparative Bioassay of Drugs in Adjuvant-Induced Arthritis in Rats: Flufenamic Acid, Mefenamic Acid, and Phenylbutazone, *Arth. Rheum.*, 12:472–482.
5. Francis, M. D., Flora, L. King, W. R. (1972), The Effects of Disodium Ethane-1—Hydroxy-1—Diphosphonate on Adjuvant Induced Arthritis in Rats, *Calcif. Tiss. Res.*, 9:109–121.
6. Flora, L. (1979), Comparative Antiinflammatory and Bone Protective Effects of Two Diphosphonates in Adjuvant Arthritis, *Arth. Rheum,* 22:340–346.

Adjuvant arthritis is a severe cellulitis and synovitis induced in male rats (either Sprague Dawley or Lewis strain) by a single subcutaneous (SC) injection of *Mycobacterium butyricum* (8 mg/ml) in mineral oil on day 0. The compounds are dosed once daily either orally (PO) or parenterally (SC) and can be tested in either prophylactic (from day 0) or therapeutic (from day 9 or 10 or 14) protocols. Antiarthritic efficacy can be measured as a reduction in paw volume, body weight loss, bone loss or reactive new bone formation compared to the saline-treated arthritic controls. Treatment can be stopped and the "flare" response (rapid increase in inflammation) examined, which indicates a compound's ability to maintain efficacy.

Materials and Methods

A. Animals

Animals used are male Lewis rats (LEW). On arrival, the rats are randomized by computer generated random numbers and placed in individual wire suspended cages. Food and water are administered ad libitum, throughout the entire study. Routine care and maintenance of the animals are performed according to State and Federal regulations. Each rat is identified with a number placed in front of the cage and on the tail of the rat.

B. Experimental Design

On day 1 body weights (BW) and hind paw volume [(PV) recorded by a mercury displacement method using a pressure transducer linked into a computer] measurements are taken on all rats. On day 0, the induction of arthritis using MFA [*Mycobacterium butyricum* (Mb) 4.4 mg/kg in oil] is as follows: rats are anesthetized and receive a single SC injection of MFA at the base of the tail under aseptic conditions.

Paw volumes and body weights are measured thereafter on various days, usually twice a week. For the prophylactic protocol, rats are randomly allocated into groups of 8–10 rats and treatment begins on day 0 and continues daily until termination. For the therapeutic protocol, the rats are randomized into treatment groups of 8–10 rats according to their PV on day 10. Dosing begins on day 10 and continues daily until termination. For both protocols, animals are placed in shoe box cages with deep bedding on or before day 10.

Dosing Solutions

Drugs are weighed out on a calibrated balance and then mixed with deoxygenated water in a volumetric flask. The stock solution is filtered through a 0.45 $\mu$m sterile filter into a sterile storage container. When not in use, the stock solution is kept refrigerated.

On a daily basis, a specific amount of solution is removed from the stock solution, put into small dosing beaker and then adjusted to pH 7.4 according to a predetermined calculation. Further dilutions of the adjusted solution can be made if necessary (with deoxygenated water).

Drug calculations are made based on the molecular weight, the purity of the compound, the amount based on mg/kg (body weight) and the desired final concentration in mgP/kg. The volume dosed per rat is 0.1 ml/100 gm of body weight subcutaneously, given as an injection in the inguinal fold of the animal, alternating sides each day or 1 ml/200 gm BW given orally using a curved stainless steel dosing tube. Adjustments based on changes in body weight are made weekly.

Radiographs, Necropsy and Tissue Collection

At termination, each rat is sacrificed with 1 ml Socomb® intraperitoneally (IP). Immediately a whole body radiograph is taken by a Torrox 120D x-ray unit at MA=5, ISUP=50 and time=60 sec. on Kodak non-screen medical film. Hind legs are removed from each rat and fixed in 10% buffered formalin along with a piece of liver, kidney, spleen, and thimus. The tibiotarsal joints are decalcified in 4% EDTA, pH 7.4 and processed routinely in paraffin blocks and H+E stain. The organ parts also processed in paraffin and stained H+E.

The histology sections are evaluated qualitatively for bone and soft tissue lesions using light microscopy. Radiographs are graded for bone resorption (BR) in 6 anatomical trabecular bone sites in each hind leg and 4 sites in each front leg on a scale of 0–3 giving an arbitrary score of 0–60 for all 4 legs. For reactive new bone formation (RNB), radiographs are graded on a severity scale of 0–3 for the lateral and medical surfaces of the tibia and then 0–2 for all other areas mentioned above, giving an arbitrary score of 0–44.

D. Statistical Analysis

Data analysis on paw volume, bone resorption and reactive new bone formation is performed by student's t-test and one-way analysis of variance with Tukeys (SAS) (12). Differences are considered significant at p=0.05 or less.

This model provides in vivo data for the efficacy of antiarthritic compounds in terms of reducing paw swelling bone loss and reactive new bone formation compared to the saline treated arthritic animals.

EXAMPLE U

Capsules are prepared by conventional methods, comprised as follows:

|  | Mg Per Capsule |
| --- | --- |
| Active Ingredient |  |
| [2-amino-1-hydroxy-3-mercapto-3-methylbutylidene]bis[phosphonic acid | 350.0 |
| Excipients |  |
| Lactose | 90.0 |
| Microcrystalline Cellulose | 60.0 |
| Magnesium Stearate | 1.0 |

The capsules having the above composition are prepared using conventional methods as described below:

The active ingredient is mixed with the microcrystalline cellulose in a turn shell blender for approximately ten (10) minutes.

The resulting mixture is passed through a hammer mill with an 80 mesh screen.

The mixture is put back into the twin shell blender along with the lactose and is then mixed for approximately fifteen (15) minutes.

The magnesium stearate is next added and blended for an additional five (5) minutes. The resulting blend is then compressed on a piston-activated capsule filler.

The above capsules administered orally twice daily for 6 months substantially reduce bone resorption in a patient weighing approximately 70 kilograms afflicted with osteoporosis. Similar results are obtained when [2-amino-1-hydroxy-3-mercapto-3-methylbutylidene]bis[phosphonic acid] in the above described capsules is replaced with any of the various compounds, or a pharmaceutically-acceptable salt or ester thereof, synthesized in Examples A–R, herein, or a pharmaceutically acceptable salt or ester of these phosphonate compounds.

EXAMPLE V

Tablets are prepared by conventional methods, formulated as follows:

|  | Mg Per Tablet |
| --- | --- |
| Active Ingredient |  |
| [2-mercapto-2-methylpropylidene]-bis[phosphonic acid] | 700.00 |
| Excipients |  |
| Lactose (spray-dried) | 200.0 |
| Starch (1500) | 100.0 |
| Magnesium Stearate | 25.0 |

Tablets are prepared having the above composition using conventional methods as described below:

The active ingredient is ground in a ball mill for approximately thirty (30) minutes. The milled active ingredient is then blended in a twinblade mixer with the spray-dried lactose for approximately twenty (20) minutes.

The starch is added to the mixture and is then mixed for an additional fifteen (15) minutes. The blend is compressed into tablets on a standard tablet press.

The above tablets administered orally twice daily for 6 months substantially reduce bone resorption in a patient weighing approximately 70 kilograms afflicted with Paget's disease.

Similar results are obtained when [2-mercapto-2-methylpropylidene]bis[phosphonic acid] in the above described tablets is replaced with any of the various compounds, or a pharmaceutically-acceptable salt or ester thereof, synthesized in Examples A–R, herein, or a pharmaceutically acceptable salt or ester of these phosphonate compounds.

EXAMPLE W

Injectable solutions are prepared by conventional methods using 10.0 ml of physiological saline solution and 7.0 mg P of [2-amino-1-hydroxy-3-mercapto-3-methylbutylidene]bis[phosphonic acid], adjusted to pH=7.4.

One injection, one time daily for 4 days, results in appreciable alleviation of hypercalcemia of malignancy in patients weighing approximately 70 kilograms.

EXAMPLE X

A Caucasian male, weighing approximately 92 kilograms, seventy-two years of age, suffers from moderate to severe pain, and occasional swelling, of the right knee. After approximately one year of steadily increasing discomfort, he visits a physician who renders a clinical diagnosis of osteoarthritis of the right knee, which was subsequently verified by X-ray diagnosis.

After a period of ameliorative therapy of various NSAIDs, including aspirin, naprosen, and ketoprofen, his symptoms continue to worsen and his condition appears to degenerate. He returns to his physician who then prescribes the capsules prepared as described in Example U twice daily two hours before or after meals for a period of three months. His clinical symptoms of pain and swelling, particularly with extended walking, improved significantly after his 3 months of therapy.

At the conclusion of three months at a dosage of 2 capsules per day, the therapy is continued at one-half the dosage originally prescribed (i.e. I capsule per day) indefinitely.

EXAMPLE Y

A black female, weighing approximately 65 kilograms, fifty-five years of age, presents with swelling and deformation of the finger joints of both hands, with partial loss of strength and/or dexterity of her fingers and hands. Upon visual and X-ray examination and various appropriate clinical tests approved by the American Rheumatological Association (ARA) she is diagnosed with rheumatoid arthritis.

After an unsuccessful analgesic and anti-inflammatory therapy, her physician prescribes the capsules prepared in Example U, two times daily two hours before or after meals for a period of four months. After a month of therapy, her symptoms of knuckle swelling noticeably improves and her range of finger motion increases significantly; she continues therapy for the remainder of the four months, after which her physician continues the prescribed dose for an additional two months.

EXAMPLE Z

A female of Hispanic origin, twelve years of age, weighing approximately 37 kilograms, presents to the physician with idiopathic juvenile rheumatoid arthritis. Her symptoms include marked inflammation of multiple joints, complicated by heat and tenderness and indicating rapid and pathological degeneration of joint function.

Her physician refers her to a rheumatologist who immediately prescribes aggressive therapy by IV administration of the solution prepared as described in Example W over a period of three days, at the rate of 1 injection per day, administered over two hours. At the conclusion of the IV regimen, the physician prescribes the capsules prepared as described in Example U, for a period of two months, during which she exhibits marked improvement with increased mobility and decreased pain. For the succeeding two months, the physician reduces her dose to ¾ of the original oral dose by prescribing 3 capsules over a period of two days, i.e. one 2-capsule day alternating with one 1-capsule day. At the conclusion of this regimen the dosage is again reduced to ¼ of the original dose by giving her the tablets prepared as described in Example V, 1 tablet every day for an additional four months.

What is claimed is:

1. Sulfur-containing phosphonate compound, or a pharmaceutically-acceptable phosphonic acid salt or ester thereof, having the following structure:

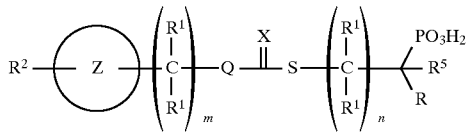

wherein m and n are integers 0 to 10 and m+n equals 0 to 10, and wherein
(a) X is O or S;
(b) Z is a covalent bond or a monocyclic or polycyclic carbocyclic ring moiety;
(c) Q is a covalent bond; O; or S;
(d) R is [COOH, SO$_3$H,]PO$_3$H$_2$ or P(O)(OH)R$^4$, wherein R$^4$ is a substituted or unsubstituted C$_1$-C$_8$ alkyl;
(e) each R$^1$ is independently selected from —SR$^6$; —R$^8$SR$^6$; nil; hydrogen; unsubstituted or substituted C$_1$-C$_8$ alkyl; monocyclic or polycyclic carbocyclic ring moiety; unsubstituted or substituted aryl; substituted or unsubstituted thiophene; substituted or unsubstituted oxathiazole; substituted or unsubstituted pyranone; substituted or unsubstituted furan; hydroxy; amido; —CO$_2$R$^3$; —O$_2$CR$^3$; —NR$^3$$_2$; —OR$^3$; —N(R$^3$)C(O)R$^3$; —C(O)N(R$^3$)$_2$; substituted or unsubstituted benzyl; nitro; or combinations thereof;
(f) R$^2$ is independently selected from —SR$^6$; —R$^8$SR$^6$; —CO$_2$R$^3$; —O$_2$CR$^3$; —C(O)N(R$^3$)$_2$; —N(R)$^3$C(O)R$^3$; —OR$^3$; nil; hydrogen; unsubstituted or substituted C$_1$-C$_8$ alkyl; unsubstituted or substituted aryl; hydroxy; substituted or unsubstituted benzyl; nitro; or combinations thereof;
(g) each R$^3$ is independently selected from hydrogen; substituted or unsubstituted C$_1$-C$_8$ alkyl; or [R$^8$SR$^6$] —R$^8$SR$^6$;
(h) R$^5$ is selected from —SR$^6$; [R$^8$SR$^6$] —R$^8$SR$^6$; hydrogen; hydroxy; amino; halogen; or unsubstituted or substituted C$_1$-C$_8$ alkyl;
(i) R$^6$ is independently selected from H, —C(O)R$^7$; or C(O)N(R$^7$)$_2$; where R$^7$ is hydrogen, or unsubstituted or substituted C$_1$-C$_8$ alkyl; and
(j) R$^8$ is substituted or unsubstituted C$_1$-C$_8$ alkyl;
provided that if Z is a covalent bond and m is 0, then R$^2$ is other than nil.

2. A compound according to claim 1, wherein Z is selected from the group consisting of phenyl, cyclopentyl, cyclohexyl and cycloheptyl.

3. A compound, according to claim 1, wherein R$^1$ is independently selected from the group consisting of hydrogen; substituted or unsubstituted C$_1$-C$_8$ alkyl; —NR$^3$$_2$; or —CO$_2$R$^3$.

4. A compound, according to claim 1, wherein R$^2$ is independently selected from the group consisting of hydrogen; hydroxy, substituted or unsubstituted C$_1$-C$_8$ alkyl; —C(O)N(R$^3$)$_2$; or —CO$_2$R$^3$.

5. A pharmaceutical composition comprised of a safe and effective amount of a compound according to claim 1 and pharmaceutically-acceptable excipients.

6. A composition according to claim 5 comprised of 0.1% to 99.9% by weight of the compound according to claim 1.

7. A composition according to claim 6 comprised of 20% to 80% by weight of the compound according to claim 1.

8. A composition according to claim 6 comprised of 15% to 95% of a compound according to claim 1; 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

9. A method of treating or preventing disorders associated with abnormal calcium and phosphate metabolism wherein a safe and effective amount of a compound according to claim 1 is administered to a human or other mammal in need of such treatment.

10. A method according to claim 9 wherein said human or other mammal is suffering from osteoporosis.

11. A method according to claim 9 wherein said human or other mammal is suffering from arthritis.

12. A method according to claim 9 wherein said human or other mammal is suffering from osteoarthritis.

13. A method according to claim 9 wherein said human or other mammal is suffering from rheumatoid arthritis.

14. A method of treating or preventing disorders associated with abnormal calcium and phosphate metabolism wherein a human or other mammal in need of such treatment is administered a pharmaceutical composition according to claim 5.

* * * * *